(12) United States Patent
Umezu

(10) Patent No.: US 8,173,788 B2
(45) Date of Patent: May 8, 2012

(54) PEPTIDE HAVING ABILITY TO ACTIVATE CANCER-RELATED GENE

(76) Inventor: Yasuiki Umezu, Sendai (JP)

( * ) Notice: Subject to any disclaimer, the term of this patent is extended or adjusted under 35 U.S.C. 154(b) by 228 days.

(21) Appl. No.: 12/504,418

(22) Filed: Jul. 16, 2009

(65) Prior Publication Data

US 2010/0015624 A1   Jan. 21, 2010

Related U.S. Application Data

(62) Division of application No. 11/486,123, filed on Jul. 14, 2006, now Pat. No. 7,579,434.

(30) Foreign Application Priority Data

Dec. 8, 2005   (JP) .................................. 2005-354589

(51) Int. Cl.
*C07H 21/02*   (2006.01)
(52) U.S. Cl. ........................ 536/23.1; 435/975; 530/327
(58) Field of Classification Search .................... None
See application file for complete search history.

(56) References Cited

FOREIGN PATENT DOCUMENTS

| EP | 1033404 A1 | 9/2000 |
|---|---|---|
| WO | 01/40276 A2 | 6/2001 |
| WO | 02/079389 A2 | 10/2002 |

OTHER PUBLICATIONS

Burgess et al., Journal of Cell Biology, vol. 111, Nov. 1990, 2129-2138.
Lazar et al., Molecular and Cellular Biology, Mar. 1988, vol. 8 No. 3 1247-1252.
Schwartz et al., Proc Natl Acad Sci USA vol. 84: 6408-6411 (1987).
Lin et al, Biochemistry USA vol. 14: 1559-1563 (1975).

*Primary Examiner* — Sheela J Huff
(74) *Attorney, Agent, or Firm* — Westerman, Hattori, Daniels & Adrian, LLP

(57) ABSTRACT

To provide a cancer diagnostic reagent for determining malignancy of a cancer patient or a cancer cell and a tendency of canceration of a healthy subject, the reagent including a peptide having an ability to activate a cancer-related gene and extracted from cell membrane surfaces of human squamous-cell carcinoma cells or including a synthetic polynucleotide encoding the peptide or a partial amino acid sequence of the peptide.

5 Claims, 6 Drawing Sheets

FIG. 2

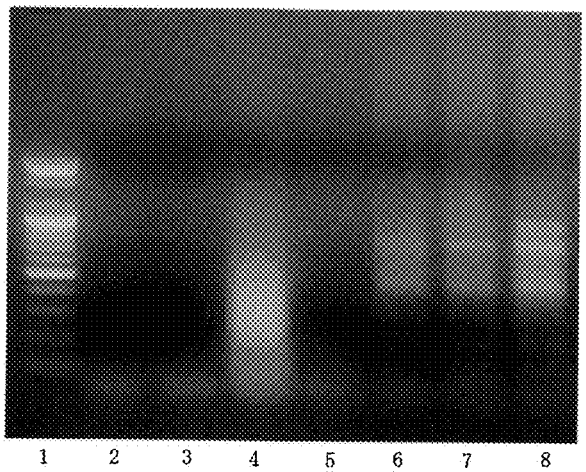

LANE 1: DNA 100 bp MARKER
LANE 2: UTC-8 CELL SAMPLE 1
LANE 3: UTC-8 CELL SAMPLE 2
LANE 4: CERVICAL CARCINOMA CELL
LANE 5: PERIPHERAL BLOOD (H.S.)
LANE 6: PERIPHERAL BLOOD (H.S.) TREATED WITH THE PEPTIDE FOR 7 HR
LANE 7: PERIPHERAL BLOOD (M.S.)
LANE 8: PERIPHERAL BLOOD (M.S.) TREATED WITH THE PEPTIDE FOR 7 HR

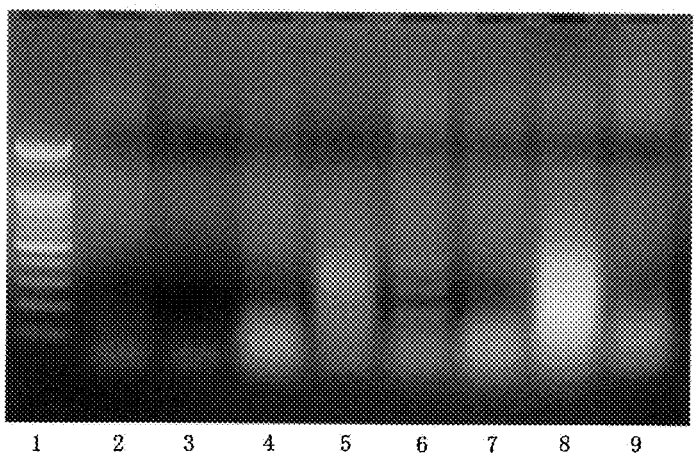

LANE 1: DNA 100 bp MARKER
LANE 2: PERIPHERAL BLOOD (E.E.)
LANE 3: PERIPHERAL BLOOD (E.E.) TREATED WITH THE PEPTIDE FOR 7 HR
LANE 4: KIDNEY MESANGIUM
LANE 5: KIDNEY MESANGIUM TREATED WITH THE PEPTIDE FOR 7 HR
LANE 6: SKIN FIBROBLAST
LANE 7: SKIN FIBROBLAST TREATED WITH THE PEPTIDE FOR 7 HR
LANE 8: PANCREATIC EPITHELIUM
LANE 9: PANCREATIC EPITHELIUM TREATED WITH THE PEPTIDE FOR 7 HR

FIG. 3

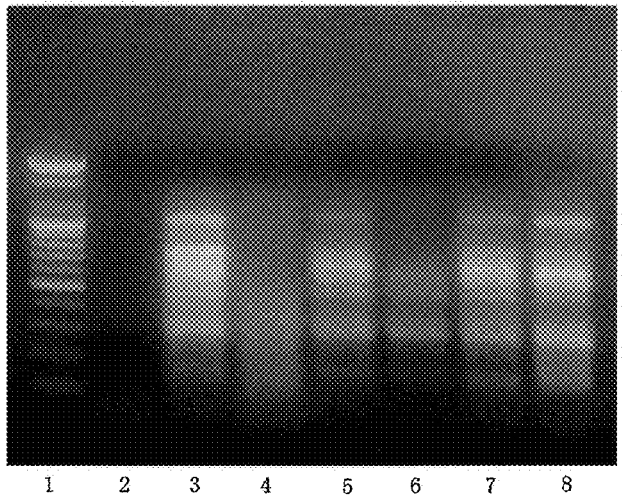

(A)

LANE 1: DNA 100 bp MARKER
LANE 2: UTC-8 CELL SAMPLE 1
LANE 3: UTC-8 CELL SAMPLE 2
LANE 4: CERVICAL CARCINOMA CELL
LANE 5: PERIPHERAL BLOOD (H.S.)
LANE 6: PERIPHERAL BLOOD (H.S.) TREATED WITH THE PEPTIDE FOR 7 HR
LANE 7: PERIPHERAL BLOOD (M.S.)
LANE 8: PERIPHERAL BLOOD (M.S.) TREATED WITH THE PEPTIDE FOR 7 HR

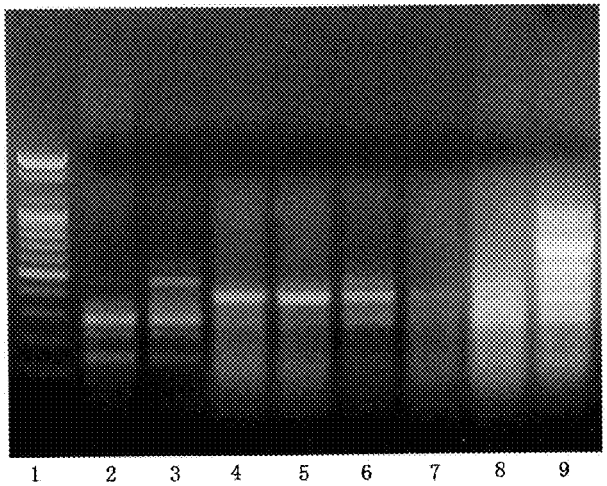

(B)

LANE 1: DNA 100 bp MARKER
LANE 2: PERIPHERAL BLOOD (E.E.)
LANE 3: PERIPHERAL BLOOD (E.E.) TREATED WITH THE PEPTIDE FOR 7 HR
LANE 4: KIDNEY MESANGIUM
LANE 5: KIDNEY MESANGIUM TREATED WITH THE PEPTIDE FOR 7 HR
LANE 6: SKIN FIBROBLAST
LANE 7: SKIN FIBROBLAST TREATED WITH THE PEPTIDE FOR 7 HR
LANE 8: PANCREATIC EPITHELIUM
LANE 9: PANCREATIC EPITHELIUM TREATED WITH THE PEPTIDE FOR 7 HR

FIG. 4

HUMAN CANCER CELLS ON WHICH THE ANTIBODY OF THE PRESENT
INVENTION SHOWED CYTOTOXIC ACTIVITY

MONOCLONAL ANTIBODY DRUG CYTOTOXIC TO CANCER CELLS

· CELL-KILLING AND CYTOTOXIC ACTIVITY AGAINST VARIOUS HUMAN CANCER CELLS

| cell | code | monoclonal antibody # |
|---|---|---|
| PANCREATIC CANCER | MIA-Pa-Ca-2 | 1 |
| LIVER CANCER | Hep3B | 13 |
| PROSTATIC CANCER | PC-3 | 1 |
| LUNG LARGE CELL CARCINOMA | COR-L23 | 13 |
| LUNG SMALL CELL CARCINOMA | COR-L279 | 2 |
| LUNG NON-SMALL CELL CARCINOMA | NCL-H727 | 1 |
| BREAST CANCER | ZR-75-30 | 10 |
| UTERINE CERVICAL CANCER | HeLa | 12 |
| OVARIAN CANCER | 59M | 4 |
| UTERINE ENDOMETRIAL CANCER | ishikawa | 5 |

HUMAN PANCREATIC CANCER CELLS STAINED WITH FITC-LABELED MONOCLONAL ANTIBODY NO. 1

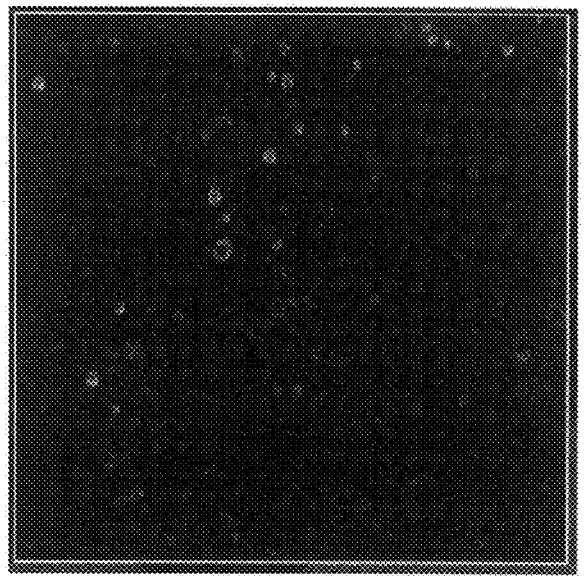

FIG. 5

THE COURSE OF REJECTION OF TRANSPLANTED SKIN GRAFT

IMMUNOSUPPRESSIVE AGENT FOR TRANSPLANTATION

・AGENT SELECTIVELY SUPPRESSING TRANSPLANTATION IMMUNITY

SUPPRESSION OF TRANSPLANTATION IMMUNITY UTILIZING SELECTIVELY SUPPRESSING ACTIVITY AGAINST CELLULAR IMMUNITY

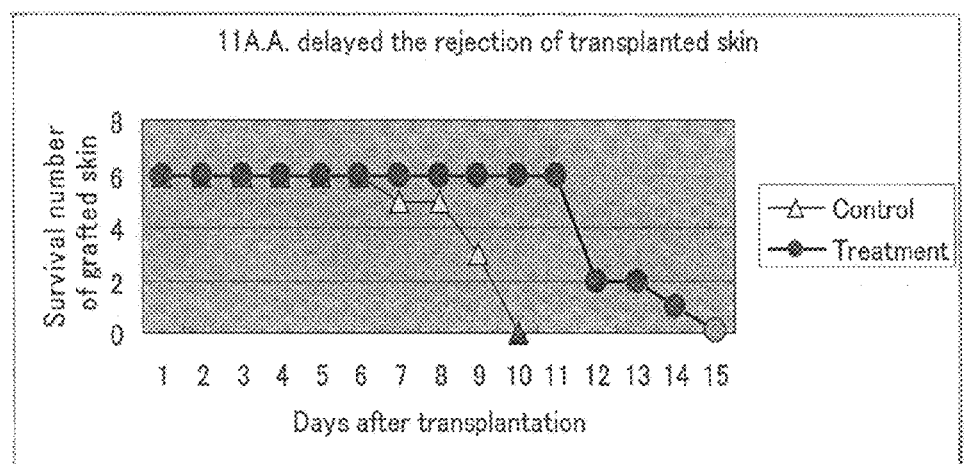

Administration amount: 50 μg/mouse each time (skin of the back of a C57Black/6N mouse was transplanted to the back of a BALB/c mouse)
Administration route: Subcutaneously administered into the neck
Administration day: On 3 subsequent days before operation and 2nd, 3rd, 7th, and 14th days after the operation

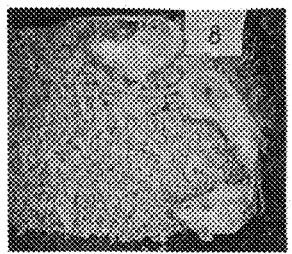

On 14th day after transplantation
(Treatment G1)

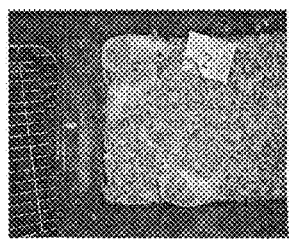

On 10th day after transplantation
(Control G1)

```
                        SEQUENCE LISTING

<160> NUMBER OF SEQ ID NOS: 17

<210> SEQ ID NO 1
  <211> LENGTH: 11
  <212> TYPE: PRT
  <213> ORGANISM: Human squamous cell carcinoma

<400> SEQUENCE: 1

Gln Pro Gln Phe Gly Arg Arg Met Glu Ser Lys
  1               5                   10

<210> SEQ ID NO 2
  <211> LENGTH: 12
  <212> TYPE: DNA
  <213> ORGANISM: Artificial
  <220> FEATURE:
  <223> OTHER INFORMATION: Primer
  <220> FEATURE:
  <221> NAME/KEY: misc_feature
  <222> LOCATION: (3)..(3)
  <223> OTHER INFORMATION: G or A
  <220> FEATURE:
  <221> NAME/KEY: misc_feature
  <222> LOCATION: (9)..(9)
  <223> OTHER INFORMATION: G or A
  <220> FEATURE:
  <221> NAME/KEY: misc_feature
  <222> LOCATION: (6)..(6)
  <223> OTHER INFORMATION: A or T or C or G
  <220> FEATURE:
  <221> NAME/KEY: misc_feature
  <222> LOCATION: (12)..(12)
  <223> OTHER INFORMATION: C or T

<400> SEQUENCE: 2
canccncant tn                                                           12

<210> SEQ ID NO 3
  <211> LENGTH: 12
  <212> TYPE: DNA
  <213> ORGANISM: Artificial
  <220> FEATURE:
  <223> OTHER INFORMATION: Primer
  <220> FEATURE:
  <221> NAME/KEY: misc_feature
  <222> LOCATION: (3)..(3)
  <223> OTHER INFORMATION: A or C or G or T
  <220> FEATURE:
  <221> NAME/KEY: misc_feature
  <222> LOCATION: (6)..(6)
  <223> OTHER INFORMATION: G or A
  <220> FEATURE:
  <221> NAME/KEY: misc_feature
  <222> LOCATION: (9)..(9)
  <223> OTHER INFORMATION: C or T
  <220> FEATURE:
  <221> NAME/KEY: misc_feature
  <222> LOCATION: (12)..(12)
  <223> OTHER INFORMATION: A or T or C or G

<400> SEQUENCE: 3
ccncanttng gn                                                           12
```

```
<210> SEQ ID NO 4
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: G or A
<220> FEATURE:
<221> NAME/KEY: misc_feature
<222> LOCATION: (12)..(12)
<223> OTHER INFORMATION: G or A
<220> FEATURE:
<221> NAME/KEY: misc_feature
<222> LOCATION: (6)..(6)
<223> OTHER INFORMATION: C or T
<220> FEATURE:
<221> NAME/KEY: misc_feature
<222> LOCATION: (9)..(9)
<223> OTHER INFORMATION: A or T or C or G

<400> SEQUENCE: 4
canttnggna gn                                                          12

<210> SEQ ID NO 5
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: C or T
<220> FEATURE:
<221> NAME/KEY: misc_feature
<222> LOCATION: (9)..(12)
<223> OTHER INFORMATION: G or A
<220> FEATURE:
<221> NAME/KEY: misc_feature
<222> LOCATION: (6)..(6)
<223> OTHER INFORMATION: A or T or C or G

<400> SEQUENCE: 5
ttnggnagna gn                                                          12

<210> SEQ ID NO 6
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: A or T or C or G
<220> FEATURE:
<221> NAME/KEY: misc_feature
<222> LOCATION: (6)..(9)
<223> OTHER INFORMATION: G or A

<400> SEQUENCE: 6
ggnagnagna tg                                                          12

<210> SEQ ID NO 7
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
```

```
<222> LOCATION: (1)..(12)
<223> OTHER INFORMATION: G orA

<400> SEQUENCE: 7
agnagnatgg an                                                            12

<210> SEQ ID NO 8
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(9)
<223> OTHER INFORMATION: G or A
<220> FEATURE:
<221> NAME/KEY: misc_feature
<222> LOCATION: (12)..(12)
<223> OTHER INFORMATION: A or T or C or G

<400> SEQUENCE: 8
agnatggant cn                                                            12

<210> SEQ ID NO 9
<211> LENGTH: 12
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: G or A
<220> FEATURE:
<221> NAME/KEY: misc_feature
<222> LOCATION: (12)..(12)
<223> OTHER INFORMATION: G or A
<220> FEATURE:
<221> NAME/KEY: misc_feature
<222> LOCATION: (9)..(9)
<223> OTHER INFORMATION: A or T or C or G

<400> SEQUENCE: 9
atggantcna an                                                            12

<210> SEQ ID NO 10
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (1)..(1)
<223> OTHER INFORMATION: unknown
<220> FEATURE:
<221> NAME/KEY: misc_feature
<222> LOCATION: (38)..(54)
<223> OTHER INFORMATION: unknown
<220> FEATURE:
<221> NAME/KEY: misc_feature
<222> LOCATION: (59)..(60)
<223> OTHER INFORMATION: unknown

<400> SEQUENCE: 10
ncagccccag tttggtagga ggatggagtc taagactnnn nnnnnnnnnn nnnnaaggnn        60

<210> SEQ ID NO 11
<211> LENGTH: 60
<212> TYPE: DNA
<213> ORGANISM: Artificial
```

```
<220> FEATURE:
<223> OTHER INFORMATION: cDNA

<400> SEQUENCE: 11
tcagccgcag tttggtagaa ggatgagttc aagctgata caaacctgca cccttctcag    60

<210> SEQ ID NO 12
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (12)..(12)
<223> OTHER INFORMATION: unknown
<220> FEATURE:
<221> NAME/KEY: misc_feature
<222> LOCATION: (38)..(41)
<223> OTHER INFORMATION: unknown

<400> SEQUENCE: 12
tcactcaaag gncggtaata cggttatcca cagaatcnnn nagggataa cgcaggaaag    60

<210> SEQ ID NO 13
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (38)..(42)
<223> OTHER INFORMATION: unknown
<220> FEATURE:
<221> NAME/KEY: misc_feature
<222> LOCATION: (54)..(54)
<223> OTHER INFORMATION: unknown
<220> FEATURE:
<221> NAME/KEY: misc_feature
<222> LOCATION: (59)..(60)
<223> OTHER INFORMATION: unknown

<400> SEQUENCE: 13
tcagcctcag tttggtagaa ggatggagtc gaagatcnnn nnaaggcaat ggcnaggann    60

<210> SEQ ID NO 14
<211> LENGTH: 60
<212> TYPE: DNA
<213> ORGANISM: Artificial
<220> FEATURE:
<223> OTHER INFORMATION: cDNA

<400> SEQUENCE: 14
tcagcctcaa tttgggagga ggatggaatc caagctgcca gaacttctga cctgagtggg    60

<210> SEQ ID NO 15
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (1)..(1)
<223> OTHER INFORMATION: unknown

<400> SEQUENCE: 15
ncagccacaa tttggtagga ggatggagtc caagtgaccg aagagcaagg ctgtccaagc    60
```

```
<210> SEQ ID NO 16
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (1)..(1)
<223> OTHER INFORMATION: unknown
<220> FEATURE:
<221> NAME/KEY: misc_feature
<222> LOCATION: (40)..(40)
<223> OTHER INFORMATION: unknown

<400> SEQUENCE: 16
ncagcctcag ttcgggagga ggatggagtc aaagaataan gtggacgccg gctgggttca       60

<210> SEQ ID NO 17
<211> LENGTH: 60
<212> TYPE: DNA
<213> ORGANISM: Artificial
<220> FEATURE:
<223> OTHER INFORMATION: cDNA
<220> FEATURE:
<221> NAME/KEY: misc_feature
<222> LOCATION: (1)..(1)
<223> OTHER INFORMATION: unknown

<400> SEQUENCE: 17
ncagccgcag tttgggagga ggtagagggt ggggtggcgg gtgcagactc ctccgctgag       60
```

PEPTIDE HAVING ABILITY TO ACTIVATE CANCER-RELATED GENE

This application is a division of U.S. patent application Ser. No. 11/486,123 filed on Jul. 14, 2006, now U.S. Pat. No. 7,579,434 issued Aug. 25, 2009, which is hereby incorporated by reference in its entirety.

BACKGROUND OF THE INVENTION

1. Field of the Invention

The present invention relates to peptides activating a cancer-related gene and derived from cell membrane surfaces of human cancer cells, immunosuppressive agents including the peptides as an effective component, and anticancer agents including antibodies against the peptides as an effective component. The present invention further relates to diagnostic reagents including polynucleotides encoding the peptides for diagnosing malignancy of cancer or tendency of canceration. Furthermore, the present invention relates to methods for manufacturing the peptides.

2. Description of the Related Art

Cancer is a disease caused by cells which started unregulated growth. The cells continue to proliferate and infiltrate into neighboring normal cells to destroy the normal functions. Some of the cells spread by metastasis from their original site to one or more sites elsewhere in the body, leading to a loss of normal cell functions and to depression of functions of organs. Thus, cancer is a disease that leads patients to death. Normal cells proliferate but will stop growing when they come in contact with solid substances (contact inhibition). On the other hand, the contact inhibition property is lost in cancerous cells. Consequently, the cancerous cells continue to grow in their host as long as the host is alive. Among cells extracted from the body, cells having ability for continuing unlimited growth can be established as a cell line. Cancer, in a broad sense, is a state of uncontrolled cell growth due to mutation of a gene, in particular, due to mutation of a gene positively or negatively regulating cell growth. Heretofore, many studies have been conducted on genes contributing to carcinogenesis or a growth mechanism and peptides or proteins relating to them (Japanese Unexamined Patent Application Publication Nos. 2003-517306 and 2000-217585).

Among peptides or proteins derived from cell membrane surfaces of human cancer cells, generally, HLA-binding peptides are particularly thought to be cancer antigens and are thought to act on immunocompetent cells as antigens, most of all, as immunogens. Additionally, it is widely known that some proteins and glycoproteins derived from cancer cells and immunocompetent cells such as macrophages isolated from a cancer-bearing living body have an immunosuppressing activity preventing the destruction of cancer cells, for example, immunosuppressive acidic protein (IAP). Such proteins and glycoproteins are clinically used for measuring the degree of immunosuppression.

Heretofore, it has been thought that cancer cell growth progresses by a mechanism due only to self division of cancerous cells. However, the rate of cancer cell growth is not constant and cancer cells rapidly proliferate at some point. Such phenomena cannot be fully explained by the conventional view only.

SUMMARY OF THE INVENTION

On the basis of the above-mentioned phenomenon that cancer rapidly progresses at some point, cancer cells have a possibility of secreting a factor outside the cancer cells. Such a factor further accelerates the cancer cell growth by acting on normal cells neighboring the cancer cells so as to activate a cancer-related gene in the normal cells. If this factor is found, not only a mechanism of progression of cancer is clarified but also a useful drug can be provided.

Namely, it is an object of the present invention to provide a factor having a function of accelerating cancer cell growth by acting on normal cells neighboring the cancer cells so that a cancer-related gene in the normal cells is activated and to provide a corresponding gene of the factor. It is another object of the present invention to develop a valuable use of the factor and its corresponding gene by verifying the factor for the cancer-related-gene-activating function in normal cells.

The present inventor has performed intensive studies for overcoming the above-mentioned problems, and, as a result, found a peptide and a gene encoding the peptide in an extract of a human squamous-cell carcinoma cell line UTC-8 which has a high activity of metastasis. Furthermore, the inventor has proved that the peptide has a function of activating a cancer-related gene in normal cells neighboring cancer cells by acting on the normal cells and accelerating cancer growth, and has proved that the peptide can be used as an immunosuppressive agent. In addition, the inventor has found that a polynucleotide capable of hybridizing with the gene encoding the peptide can be used as a reagent for diagnosing malignancy of cancer or measuring tendency of canceration (easiness of conversion to cancer: a degree of risk of canceration), which was not included in clinical examination items before, and that an antibody against the peptide has an anticancer activity. Thus, the present invention has been accomplished.

The present invention relates to aspects (1) to (10) described below:

(1) A peptide having an ability to activate a cancer-related gene, wherein the peptide is derived from cell membrane surfaces of human squamous-cell carcinoma cells and includes an amino acid sequence represented by SEQ ID No: 1 or an amino acid sequence having deletion, substitution, or addition of one or several amino acids in the amino acid sequence represented by SEQ ID NO: 1;

(2) A peptide having an ability to activate a cancer-related gene, wherein the peptide is derived from cell line UTC-8 (FERM BP-08611) established from human squamous-cell carcinoma; and the peptide shows a detectable peak at a detection wavelength of 214 nm in gel filtration of an extract from the cell line;

(3) An immunosuppressive agent comprising the peptide according to the aspect (1) or (2) as an effective component;

(4) An antibody against the peptide according to the aspect (1) or (2);

(5) A diagnostic reagent including the antibody according to the aspect (4) for determining tendency of canceration or malignancy of cancer;

(6) An anticancer agent comprising the antibody according to the aspect (4) as an effective component;

(7) A polynucleotide including a nucleotide sequence encoding at least three contiguous amino acids of the amino acid sequence of the peptide according to the aspect (1);

(8) A diagnostic kit for determining tendency of canceration or malignancy of cancer, wherein the kit includes a peptide according to the aspect (1) or (2) and a polynucleotide according to the aspect (7);

(9) The diagnostic kit according to the aspect (8) further including at least one marker gene selected from the group consisting of:

Ras oncogene family;

v-crk avian sarcoma virus CT10 oncogene homolog-like lactate dehydrogenase B;

Placental growth factor;
Interleukin 8;
MAS1, activator of S phase kinase;
v-raf;
v-fms;
v-rel;
v-src;
GRO1;
Hepatoma-derived growth factor;
Vascular endothelial growth factor;
Bone morphogenic protein 3;
Squamous-cell carcinoma antigen recognized by T cell;
Interleukin-1 beta;
Conserved gene amplified in osteosarcoma; and
Lymphoid blast crisis oncogene; and

(10) A method for preparing a peptide according to the aspect (1) or (2), the method including the steps of immersing cells obtained by culturing human squamous-cell carcinoma cells in a culture medium into a citrate-phosphate buffer having a pH of 3.3 to 3.4 for extraction; and fractionating the extract by gel filtration using a citrate-phosphate buffer having a pH of 6.8 to 7.0 for yielding a peptide having an ability to activate a cancer-related gene in human normal cells.

The peptide according to the present invention is derived from cell membrane surfaces of human squamous-cell carcinoma cells. In particular, the peptide is extremely remarkable in the fact that it has ability to activate a cancer-related gene in human normal cells. Since the sensitivity of cells and tissues against this peptide of the present invention can be an indicator to predict canceration tendency of normal cells or progress of cancer, the peptide can be a useful diagnostic reagent for determining tendency of canceration or malignancy of cancer. Additionally, it is strongly suggested that the unregulated growth of cancer cells is caused by, not only cancer cells themselves, but also the interaction accompanying the activation of various cancer-related genes in normal cells. Thus, an entirely novel mechanism of cancer growth is presented.

Therefore, the present invention can contribute greatly to the research and development of diagnosis and therapy of cancer.

BRIEF DESCRIPTION OF THE DRAWINGS

FIG. 1A shows elution patterns of the peptides by using a citrate-phosphate buffer having a pH of 7.2 as an elution buffer and detection wavelengths of 280 nm and 210 nm. FIG. 1B shows elution patterns of the fraction (elution volume: 21 ml) of the rightmost peak of the elution pattern using the detection wavelength of 280 nm in FIG. 1A by using a citrate-phosphate buffer having a pH of 6.8 as an elution buffer and detection wavelengths of 280 nm and 214 nm.

FIGS. 2A and 2B are electrophoresis photographs showing gene pattern changes in cells treated with a peptide of the present invention which were investigated by conducting a PCR reaction using cDNA prepared by reverse transcription of total mRNA derived from the cells treated with the peptide as a template and using DNA encoding the full length of the peptide of the present invention as a primer.

FIGS. 3A and 3B are electrophoresis photographs showing gene pattern changes in cells treated with a peptide of the present invention. The gene was prepared by a PCR reaction using cDNA prepared by reverse transcription of total mRNA derived from the cells treated with the peptide as a template and using DNA encoding a sequence consisting of the first to seventh amino acids of the peptide of the present invention as a primer.

FIG. 4 is a photograph showing the result when the monoclonal antibody against the peptide of the present invention was subjected to a cytotoxic test using cancer cells.

FIG. 5 is a diagram showing an immunosuppressive activity of the peptide of the present invention in a transplantation test.

DESCRIPTION OF THE PREFERRED EMBODIMENTS

Figure 1:
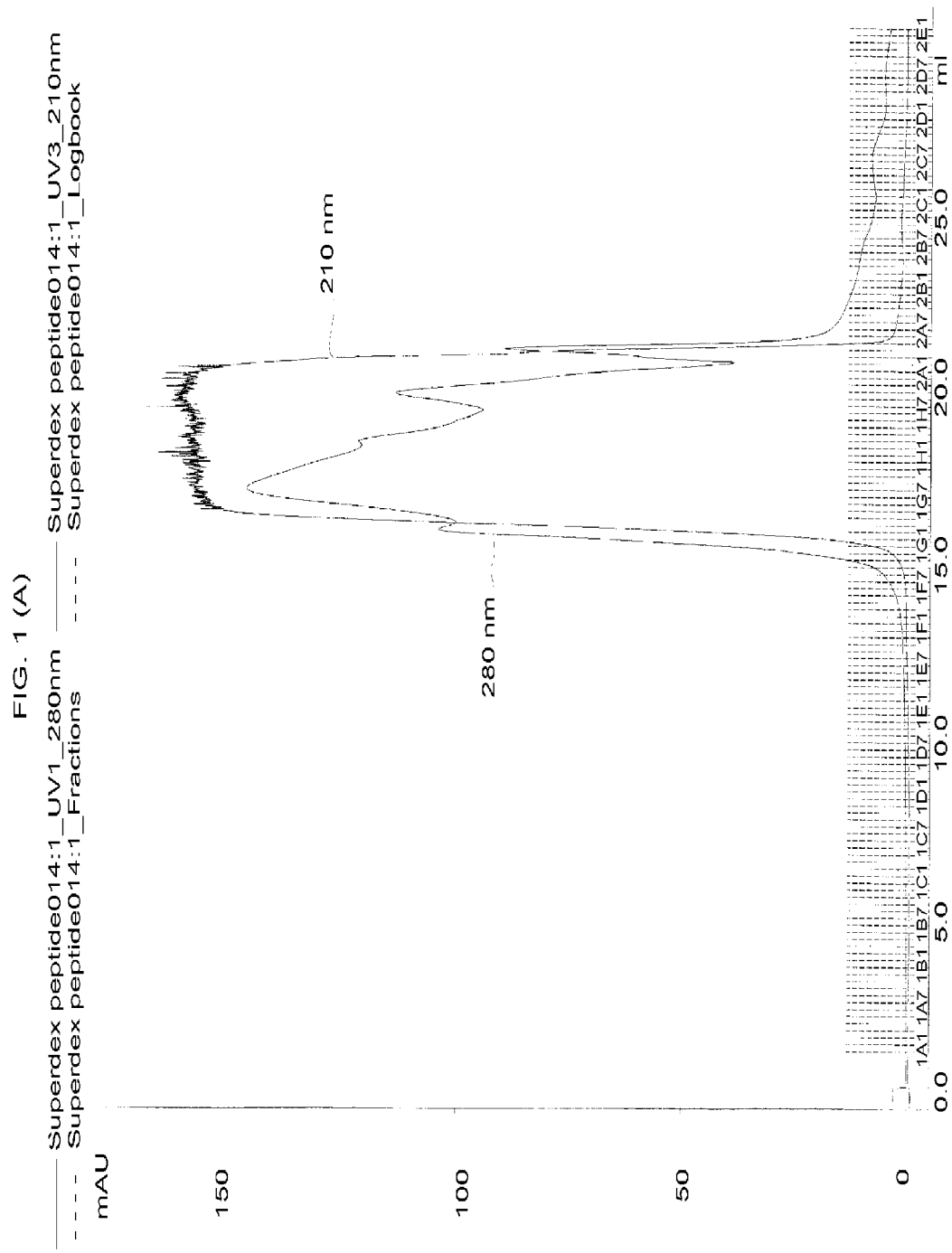
FIGS. 1A and 1B are elution patterns of gel filtration of peptides extracted in Example 1 according to the present invention.
Figure 1:
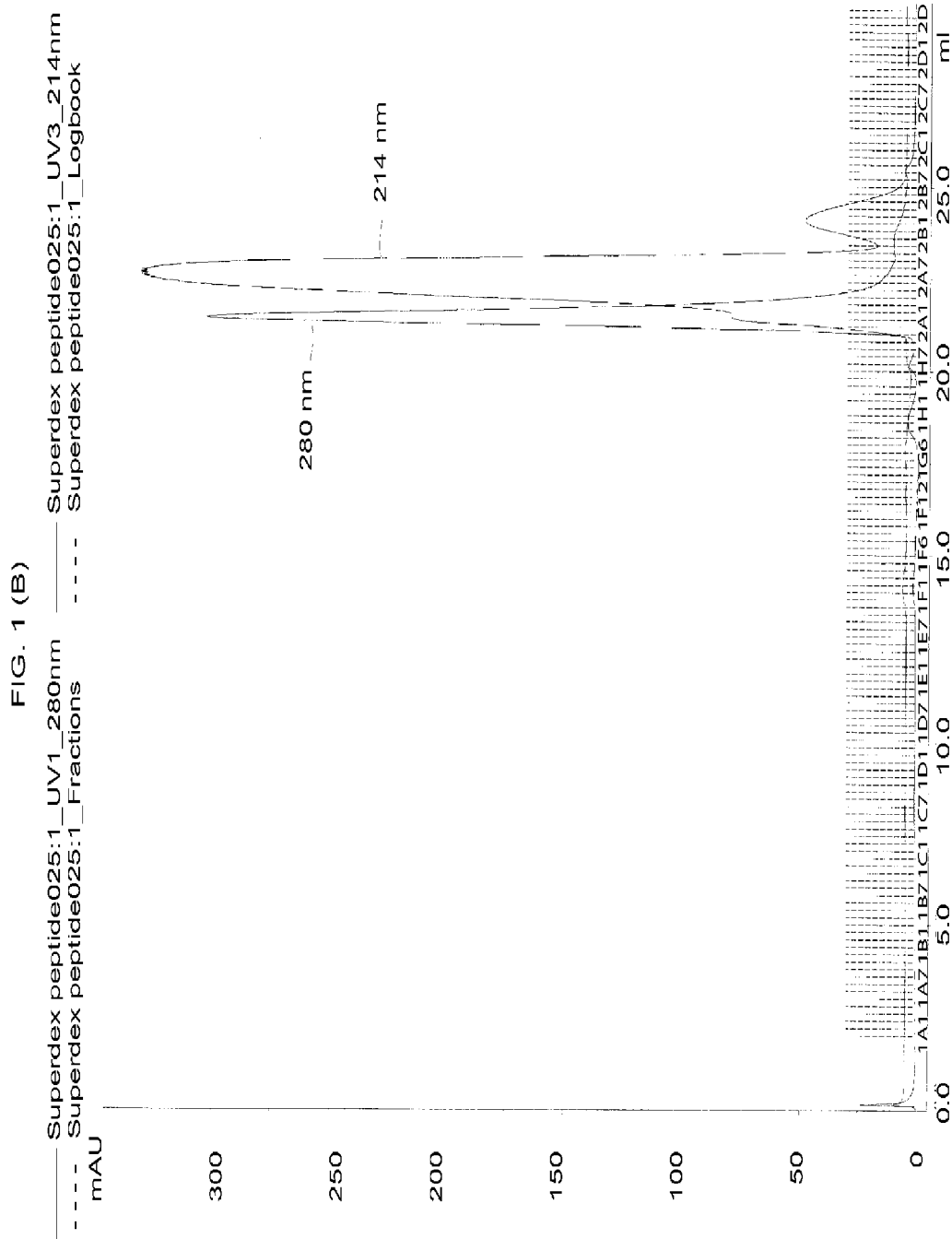

The peptide according to the present invention has a function of activating a human cancer-related gene and includes the following amino acid sequence:
Gln-Pro-Gln-Phe-Gly-Arg-Arg-Met-Glu-Ser-Lys (SEQ ID NO: 1)

Additionally, a peptide including an amino acid sequence having deletion, substitution, or addition of one or several amino acids in the amino acid sequence represented by SEQ ID NO: 1 is included in the present invention as long as the peptide has the function of activating a cancer-related gene.

The above-mentioned cancer-related gene refers to not only oncogenes but also immune system genes. The activation of a cancer-related gene means acceleration of canceration or cancer growth through activation of an oncogene or through inactivation of a tumor suppressor gene and/or activation or inactivation of an immune system gene, e.g., a cellular immunity system and/or humoral immunity system.

The immunosuppressive activity of the peptide according to the present invention is notable. For example, it is recognized that the peptide suppresses the rejection in tissue transplantation. Therefore, the peptide of the present invention can be used as an immunosuppressive agent.

The peptide represented by SEQ ID NO: 1 is derived from cell membrane surfaces of human squamous-cell carcinoma cells and can be extracted from human squamous-cell carcinoma cell line UTC-8 (Deposition No.: FERM BP-08611, which is deposited with International Patent Organism Depositary, National Institute of Advanced Industrial Science and Technology, Central 6, 1-1-1 Higashi, Tsukuba-shi, Ibaraki-ken, 305-8566, Japan, on Feb. 4, 2004) by using a citrate-phosphate buffer having a pH of 3.3 to 3.4.

More specifically, after the extraction by the citrate-phosphate buffer having a pH of 3.3 to 3.4, the extract is further applied to gel filtration using a citrate-phosphate buffer having a pH of 6.8 to 7.2 as an elution buffer at a column flow rate of 0.1 to 0.28 ml/min, and then a fraction having a peak in a detection wavelength of 214 nm is isolated to yield the peptide represented by SEQ ID NO: 1.

The peptide represented by SEQ ID NO: 1 of the present invention is characterized by the fact that the peak can be separated and detected only when a detection wavelength of 214 nm is used. The peak of the peptide of the present invention cannot be detected when a detection wavelength of 254 to 257 nm or of 280 nm, which are generally used in peptide detection, is used.

In addition to the above-mentioned extraction method, the peptide according to the present invention can be prepared by conventional chemical synthesis of peptides on the basis of the amino acid sequence. Namely, an amino acid derivative having a carboxyl group and a side-chain functional group being protected by a protecting group and an amino acid derivative having an amino group and a side-chain functional group being protected by a protecting group are condensed in the presence of carbodiimide or the like. Then, the protecting group for the amino group is removed to bind a next amino acid derivative protected by a protecting group. Such a reaction can be performed by a liquid-phase method or a solid-phase method. In general, the solid-phase method is used, except when a relatively large amount of peptide is synthesized. Particularly, in a method developed for identifying an antigenic determinant defined by its amino acid sequence, a spacer arm having an amino group on its tip is used. The spacer arm is prepared by chemically treating a cellulose film or the tip of a plastic pin. In the latter method, a peptide chain is extended by sequential reactions of solutions in a 96-well plate; this method is called multi-pin peptide synthesis.

Furthermore, in another method, a peptide of the present invention may be prepared by chemically synthesizing a DNA encoding the peptide by using a DNA synthesizer; preparing a recombinant vector by connecting the DNA to an appropriate expression vector; introducing the vector into a host such as *Escherichia coli*; culturing the host; and collecting the peptide of the present invention from the culture.

The peptide of the present invention is useful by itself and can be used as a diagnostic reagent for determining tendency of canceration (easiness of conversion to cancer: a degree of risk of canceration) of normal cells or tissues, for determining whether or not a subject is suffering from cancer, and for determining malignancy of cancer.

The above-mentioned various determinations are performed by bringing the peptide of the present invention in contact with a human cell or tissue specimen obtained by surgical resection or biopsy, and utilizing this contact for detecting a cancer-related gene or for determining a change in the expression degree or the expression pattern of the gene. The sensitivity of cells or tissues against the peptide of the present invention reflects, for example, a tendency of canceration (easiness of conversion to cancer: a degree of risk of canceration) of the cells or tissues or a degree of malignancy of cancer.

In the determination of the degree of malignancy of cancer cells or tissues, the amount of expression of the gene encoding the peptide of the present invention may be directly determined without the contact of the peptide of the present invention with the cells or tissues. However, it is desirable that the cancer cells or tissues are brought into contact with the peptide of the present invention, in order to achieve higher sensitivity in measurement.

Additionally, as is clear in diagnosis methods 1 and 2 described below, a polynucleotide (DNA and RNA) encoding at least three contiguous amino acids of the amino acid sequence of the peptide of the present invention can be used as a diagnostic reagent for determining tendency of canceration (easiness of conversion to cancer: a degree of risk of canceration) of normal cells or tissues, for determining whether or not a subject is suffering from cancer, and for determining malignancy of cancer. A diagnostic kit of the present invention preferably utilizes such a polynucleotide in combination with a peptide of the present invention.

Diagnosis methods using the peptide of the present invention will now be described.

[Diagnosis Method 1]

First, a specimen such as cells and tissues obtained from a subject to be tested is brought into contact with the peptide of the present invention, and they are cultured for a predetermined period of time. Examples of the specimen include cells and tissues obtained from a high risk group for cancer, such as subjects living in area polluted with a chemical or radioactive material and smokers; cells and tissues which are suspected to be a precancerous stage, such as polyp; cells and tissues neighboring cancer cells; cells and tissues at a region under a danger of metastasis of cancer; and peripheral blood.

When the specimen has a tendency of canceration, even if the cells and tissues are normal now, a change in an expression pattern of the gene is observed: the gene encoding the peptide of the present invention is detected, or the amount of expression of the gene is increased. When the malignancy of cancer is high, the amount of expression of the gene is further increased. Therefore, the tendency of canceration or malignancy of cancer can be determined by detecting the gene or determining the degree of its expression.

In this diagnosis method, the cells or tissues of interest are brought into contact with the peptide, and then total mRNA is extracted from the cells or tissues. After synthesis of cDNA by reverse transcription using the mRNA as a template, PCR is further conducted by using the resulting cDNA as a template. In the latter PCR, all polynucleotides encoding sequences consisting of at least three contiguous amino acid residues of the amino acid sequence represented by SEQ ID NO: 1 are collectively used as primers. The polynucleotide may encode the full-length polypeptide.

This diagnosis method will now be specifically described.

First, total mRNA is extracted by a common method from a specimen which is prepared by treating normal tissues or cells with the peptide. Then, cDNA is synthesized by reverse transcription using the total mRNA as templates to generate a cDNA pool which will be used as templates.

DNA encoding a sequence consisting of, for example, the first to fourth amino acids in the amino acid sequence represented by SEQ ID NO: 1 has the following nucleotide sequence:

CAR CCN CAR TTY (SEQ ID NO:2)

(wherein N is A, T, C, or G, R is G or A, and Y is C or T). Each of the nucleotide sequences, i.e., 32 types of DNA, is synthesized, and a pool including each DNA in an equal amount is used as forward primers.

Since the cDNA used as the template has a poly-T sequence corresponding to poly-A tailing of mRNA, an oligo-dT primer (poly-A primer) is used as a reverse primer.

The PCR using the cDNA pool as the templates is conducted by using the above-mentioned forward primers and the reverse primer, followed by electrophoresis and fluorescence staining.

When a change in an expression pattern of genes including the gene encoding the peptide of the present invention is induced by treating a specimen with the peptide of the present invention, it is indicated that the specimen is sensitive to the treatment with the peptide of the present invention; thus, it is determined that the specimen has a high tendency of canceration even if the cells or tissues as the specimen are currently normal. When a specimen is already cancerous, a change in the gene expression pattern increases with a degree of the malignancy. Therefore, the degree of the malignancy can be determined by measuring the change.

The amount of the peptide expression can be determined by measuring the fluorescence intensity of the band in the electrophoresis. In order to precisely determine the amount of the peptide expression, for example, quantitative PCR may be performed.

The quantitative PCR can be performed by, for example, real-time PCR using the cDNA pool as templates, the above-mentioned primers, and a fluorescent dye or a fluorescence-labeled probe which binds with double-strand DNA. Then, a relationship between the number of the PCR cycles and the fluorescence intensity is determined. By comparing the results with those obtained by using a standard, the amount of the cDNA, i.e., the expression amount of the peptide of the present invention, can be quantitatively determined.

A change in the gene expression pattern or an increase in the peptide expression amount can be determined by comparing the expression level of a control. As the control, the results obtained by conducting the same procedure as above using the same cells except that the peptide of the present invention is not used and/or the results obtained by treating normal cells or tissues that are completely free from cancer risk with the peptide and conducting the same procedure as above, are used.

The normal cells and tissues that are free from cancer risk are derived from young subjects. As such cells, for example, a kidney mesangium cell (ACBRI-1376; Applied Cell Biology Research Institute), a skin fibroblast cell (Catlog 2F0-C25; Cell Systems), and a pancreatic epithelial cell (CBRI515; Applied Cell Biology Research Institute) are commercially available.

From the views described above, it is obvious that a combination of the peptide of the present invention and the group of the above-mentioned primers, i.e., the group of polynucleotides encoding sequences consisting of at least three contiguous amino acid residues of the amino acid sequence represented by SEQ ID NO: 1, is useful as a cancer diagnostic reagent kit for determining a tendency of canceration or malignancy of cancer.

[Diagnosis Method 2]

In another diagnosis method using the peptide of the present invention, cancer-related gene is used as a marker gene.

In this diagnosis method, cells or tissues of interest are treated with the peptide of the present invention as in the above-mentioned diagnosis method 1; thus the same specimen as in the diagnosis method 1 can be used. However, in this diagnosis method, the reverse transcription is conducted to generate a cDNA (first-strand cDNA) pool, which is complementary to the mRNA, by using total mRNA extracted from the cells or tissues treated with the peptide as a template and using oligo-dT primer having T7 RNA polymerase promoter region as a reverse primer. Then, after the second-strand cDNA synthesis, in vitro transcription (IVT) was conducted using T7 RNA polymerase and biotinylated rNTPs at 37° C. for 14 hr to yield biotin-labeled cRNA. The amount of the cRNA is measured with a spectrophotometer to confirm that at least 10 μL of cRNA can be yielded.

The diagnosis method further includes processes for bringing this cRNA labeled with fluorescence dye or the like into contact with cDNA of a cancer-related gene which is immobilized on a plate for hybridization and for measuring the fluorescence intensity.

When the cRNA is hybridized to some cancer-related gene, it is suggested that the cancer-related gene is being expressed in the cells or tissues. When the fluorescence intensity of some cancer-related gene is increased or decreased, it is suggested that the expression amount of the cancer-related gene is increased or decreased by the treatment with the peptide of the present invention. Namely, for example, when the expression of an oncogene is increased or the expression of an immune system gene which suppresses canceration is decreased, it is suggested that the tendency of canceration is high. Thus, on the basis of the expression condition of a cancer-related gene, a tendency of canceration or malignancy of cancer can be determined.

An increase or decrease in the expression amount of a cancer-related gene is determined by comparing the expression level in a control. The cells and tissues used as the control are the same as those used in the diagnosis method 1.

As described above, immune system genes relating to cancer, in addition to oncogenes, are included in the cancer-related genes in this specification. Examples of such genes are as follows:

Ras oncogene family;
v-crk avian sarcoma virus CT10 oncogene homolog-like lactate dehydrogenase B;
Placental growth factor;
Interleukin 8;
MAS1, activator of S phase kinase;
v-raf;
v-fms;
v-rel;
v-src;
GRO1;
Hepatoma-derived growth factor;
Vascular endothelial growth factor;
Bone morphogenic protein 3;
Squamous-cell carcinoma antigen recognized by T cell;
Interleukin-1 beta;
Conserved gene amplified in osteosarcoma; and
Lymphoid blast crisis oncogene.

At least one gene of these cancer-related genes is used in this invention. For higher precision, yet more cancer-related genes may be used. In such a case, it is preferable to use a combination of genes in the following groups as a genes set for diagnosis.

(a) Oncogene expression-increasing group: a gene encoding the peptide of the present invention and Ras oncogene and c-fos oncogene, etc.;

(b) Immune gene expression-increasing group: Interleukin-1 beta, etc.; and (c) Immune gene expression-decreasing group: MHC class II, DM, and alpha, beta protein gene and killer cell lectin-like receptor subfamily B, M member 1 gene.

Tables 1 and 2 show examples of cancer-related genes of which expression is increased and immune system genes of which expression is increased or decreased by the treatment with the peptide (HPLC-purified peptide) derived from cell membrane surfaces of human squamous-cell carcinoma cells UTC-8 (Deposition No.: FERM BP-08611, which is deposited with International Patent Organism Depositary, National Institute of Advanced Industrial Science and Technology).

TABLE 1

| Cancer-related gene enhanced by the HPLC-purified peptide | | | | | | | |
|---|---|---|---|---|---|---|---|
| Gene Name | Fold Change | Common | Description | Product | Phenotype | Function | Keywords |
| K03218 | 3.912448639 | SRC; ASV; SRC1; c-SRC; p60-Src | v-src sarcoma (Schmidt-Ruppin A-2) viral | proto-oncogene tyrosine-protein kinase SRC | Colon cancer, advanced | | c-myc proto-oncogene; proto-oncogene; |

TABLE 1-continued

Cancer-related gene enhanced by the HPLC-purified peptide

| Gene Name | Fold Change | Common | Description | Product | Phenotype | Function | Keywords |
|---|---|---|---|---|---|---|---|
| | | | oncogene homolog (avian) | | | | src gene; src oncogene |
| NM_001201 | 3.73617959 | BMP3 | bone morphogenetic protein 3 (osteogenic) | bone morphogenetic protein 3 (osteogenic) precursor | | | |
| D16431 | 3.595973492 | HDGF | hepatoma-derived growth factor (high-mobility group protein 1-like) | hepatoma-derived growth factor (high-mobility group protein 1-like) | | | hepatoma-derived GF; hepatoma-derived growth factor |
| X54936 | 3.576227427 | PGF | placental growth factor, vascular endothelial growth factor-related protein | placental growth factor, vascular endothelial growth factor-related protein | | | placenta growth factor |
| M95712 | 3.033826351 | BRAF | v-raf murine sarcoma viral oncogene homolog B1 | v-raf murine sarcoma viral oncogene homolog B1 | Adenocarcinoma of lung, somatic; Colorectal cancer, somatic; Melanoma, melignant, somatic; Nonsmall cell lung cancer, somatic | | b-raf oncogene; serine/threonine protein kinase |
| NM_005850 | 3.023255825 | SF3B4 | splicing factor 3b, subunit 4, 49 kDa | splicing factor 3b, subunit 4 | | | |
| NM_005937 | 2.995664358 | MLLT6 | myeloid/lymphoid or mixed-lineage leukemia (trithorax homolog, *Drosophila*); translocated to, 6 | myeloid/lymphoid or mixed-lineage leukemia (trithorax homolog, *Drosophila*); translocated to, 6 | | | |
| NM_001419 | 2.950166225 | ELAVL1 | ELAV (embryonic lethal, abnormal vision, *Drosophila*)-like 1 (Hu antigen R) | ELAV-like 1 | | | |
| NM_002613 | 2.86612194 | PDPK1 | 3-phosphoinositide dependent protein kinase-1 | 3-phosphoinositide dependent protein kinase-1 | | protein kinase | |
| NM_014308 | 2.849243879 | P101-PI3K | phosphoinositide-3-kinase, regulatory subunit, polypeptide p101 | phosphoinositide-3-kinase, regulatory subunit, polypeptide p101 | | | |
| D26120 | 2.833239079 | | splicing factor 1 | | | | |

TABLE 1-continued

Cancer-related gene enhanced by the HPLC-purified peptide

| Gene Name | Fold Change | Common | Description | Product | Phenotype | Function | Keywords |
|---|---|---|---|---|---|---|---|
| X61498 | 2.832505941 | NFKB2 | nuclear factor of kappa light polypeptide gene enhancer in B-cells 2 (p49/p100) | nuclear factor of kappa light polypeptide gene enhancer in B-cells 2 (p49/p100) | | | NF-kb subunit |
| X03663 | 2.780905962 | CSF1R | colony stimulating factor 1 receptor, formerly McDonough feline sarcoma viral (v-fms) oncogene homolog | colony stimulating factor 1 receptor precursor | Myeloid malignancy, predisposition to | | c-fms oncogene; fms oncogene; glycoprotein; membrane protein; proto-oncogene; signal peptide |
| NM_004204 | 2.756244421 | PIGQ | phosphatidylinositol glycan, class Q | phosphatidylinositol glycan, class Q isoform 2; phosphatidylinositol glycan, class Q isoform 1 | | | |
| NM_003017 | 2.741738006 | SFRS3 | splicing factor, arginine/serine-rich 3 | splicing factor, arginine/serine-rich 3 | | | |
| NM_000753 | 2.7408638 | PDE3B | phosphodiesterase 3B, cGMP-inhibited | phosphodiesterase 3B, cGMP-inhibited | | | |
| NM_002712 | 2.696629047 | PPP1R7 | protein phosphatase 1, regulatory subunit 7 | protein phosphatase 1, regulatory subunit 7 | | regulatory polypeptide of protein phosphatase-1 | |
| NM_004906 | 2.543901205 | WTAP | Wilms tumor 1 associated protein | Wilms' tumour 1-associating protein isoform 1; Wilms' tumour 1-associating protein isoform 2 | | | |
| NM_005207 | 2.497231245 | CRKL | v-crk sarcoma virus CT10 oncogene homolog (avian)-like | v-crk sarcoma virus CT10 oncogene homolog (avian)-like | | | |
| NM_007279 | 2.493814707 | U2AF2 | U2 small nuclear ribonucleoprotein auxiliary factor (65 kD) | U2 small nuclear ribonucleoprotein auxiliary factor (65 kD) | | | |
| NM_015714 | 2.480620146 | G0S2 | putative lymphocyte G0/G1 switch gene | putative lymphocyte G0/G1 switch gene | | | |
| NM_001511 | 2.476593256 | CXCL1 | chemokine (C—X—C motif) ligand 1 (melanoma growth stimulating activity, alpha) | chemokine (C—X1—C motif) ligand 1 | | | |
| NM_016263 | 2.465854406 | FZR1 | Fzr1 protein | Fzr1 protein | | | |
| NM_012103 | 2.459948301 | AUP1 | ancient ubiquitous protein 1 | ancient ubiquitous protein 1 isoform 1; ancient ubiquitous protein 1 isoform 2; | | | |

TABLE 1-continued

Cancer-related gene enhanced by the HPLC-purified peptide

| Gene Name | Fold Change | Common | Description | Product | Phenotype | Function | Keywords |
|---|---|---|---|---|---|---|---|
| | | | | ancient ubiquitous protein 1 isoform 3 | | | |
| M32977 | 2.456767944 | VEGF | vascular endothelial growth factor | vascular endothelial growth factor | Diabetic retinopathy, NIDDM-related, susceptibility to | | angiogenic mitogen; vascular endothelial growth factor |
| NM_007040 | 2.432915688 | E1B-AP5 | E1B-55 kDa-associated protein 5 | E1B-55 kDa-associated protein 5 isoform a; E1B-55 kDa-associated protein 5 isoform d; E1B-55 kDa-associated protein 5 isoform b; E1B-55 kDa-associated protein 5 isoform c | | | |
| NM_001402 | 2.404632807 | EEF1A1 | eukaryotic translation elongation factor 1 alpha 1 | eukaryotic translation elongation factor 1 alpha 1 | | | |
| NM_002357 | 2.396934271 | MAD | MAX dimerization protein 1 | MAX dimerization protein 1 | | | |
| NM_005524 | 2.39485383 | HES1 | hairy and enhancer of split 1, (Drosophila) | hairy and enhancer of split 1 | | | |
| NM_005730 | 2.387011766 | CTDSP2 | conserved gene amplified in osteosarcoma | nuclear LIM interactor-interacting factor 2 | | | |
| AF040963 | 2.356589317 | MXD4 | MAX dimerization protein 4 | MAD4 | | | |
| M83221 | 2.351067066 | RELB | v-rel reticuloendotheliosis viral oncogene homolog B, nuclear factor of kappa light polypeptide gene enhancer in B-cells 3 (avian) | reticuloendotheliosis viral oncogene homolog B | | NF-kappa-B transcpription factor p50-subunit inhibitor | I-Rel; NF-kappa-B transcription factor inhibitor |
| NM_006842 | 2.24469161 | | splicing factor 3b, subunit 2, 145 kDa | | | | |
| NM_001570 | 2.239902258 | IRAK2 | interleukin-1 receptor-associated kinase 2 | interleukin-1 receptor-associated kinase 2 | | | |
| NM_006716 | 2.230443954 | ASK | activator of S phase kinase | activator of S phase kinase | | | |
| NM_004723 | 2.209302187 | ARHGEF2 | rho/rac guanine nucleotide exchange factor (GEF) 2 | rho/rac guanine nucleotide exchange factor 2 | | | |
| M60119 | 2.204995632 | HIVEP2; MBP-2; HIV-EP2 | human immunodeficiency virus type I enhancer binding protein 2 | human immunodeficiency virus type I enhancer binding protein 2 | | | |
| NM_001665 | 2.111301422 | ARHG | ras homolog gene | ras homolog gene family, member G (rho | | | |

TABLE 1-continued

Cancer-related gene enhanced by the HPLC-purified peptide

| Gene Name | Fold Change | Common | Description | Product | Phenotype | Function | Keywords |
|---|---|---|---|---|---|---|---|
| | | | family, member G (rho G) | G) | | | |
| M62829 | 2.104651213 | EGR1 | early growth response 1 | early growth response 1 | | | transcription factor |
| NM_004218 | 2.102017164 | RAB11B | RAB11B, member RAS oncogene family | RAB11B, member RAS oncogene family | | | |
| NM_006318 | 2.098191261 | | putative glialblastoma cell differentiation-related | | | | |
| U33819 | 2.0930233 | MAZ | MYC-associated zinc finger protein (purine-binding transcription factor) | MYC-associated zinc finger protein | | | |
| M13150 | 2.069767475 | MAS1 | MAS1 oncogene | MAS1 oncogene | | | mas oncogene; mas protein; membrane protein; proto-oncogene |
| NM_003685 | 2.039983511 | KHSRP | KH-type splicing regulatory protein (FUSE binding protein 2) | KH-type splicing regulatory protein (FUSE binding protein 2) | | | |
| NM_006694 | 2.018802404 | JTB; PAR; hJT; HJTB; B PAR | jumping translocation breakpoint | jumping translocation breakpoint | | | |
| NM_006191 | 2.002365112 | PA2G4 | proliferation-associated 2G4, 38 kDa | proliferation-associated 2G4, 38 kDa | | | |
| X78710 | 2.001409531 | MTF1 | metal-regulatory transcription factor 1 | metal-regulatory transcription factor 1 | | | metal-regulatory transcription factor; MTF-1 gene; transcription factor |

TABLE 2

Immune system gene regulated by the HPLC-purified peptide

| | Gene Name | TDP | Description | Product | Phenotype | function | Keywords |
|---|---|---|---|---|---|---|---|
| | | | | Immune system gene enhanced by the peptide | | | |
| 1 | K02770 | 11.69 | interleukin 1, beta | interleukin 1, beta proprotein | | interleukin-1 receptor binding; signal transducer activity | interleukin; interleukin 1 |
| 2 | J04130 | 7.341 | chemokine (C-C motif) ligand 4 | chemokine (C-C motif) ligand 4 precursor | | receptor signaling protein | act2 gene; immune |

TABLE 2-continued

Immune system gene regulated by the HPLC-purified peptide

| | Gene Name | TDP | Description | Product | Phenotype | function | Keywords |
|---|---|---|---|---|---|---|---|
| | | | | | | tyrosine kinase activity; chemokine activity | activation gene |
| 3 | NM_000211 | 3.326 | integrin, beta 2 (antigen CD18 (p95), lymphocyte function-associated antigen 1; macrophage antigen 1 (mac-1) beta subunit) | integrin beta chain, beta 2 precursor | Leukocyte adhesion deficiency | cell adhesion receptor activity | |
| 4 | X03663 | 2.781 | colony stimulating factor 1 receptor, formerly McDonough feline sarcoma viral (v-fms) oncogene homolog | colony stimulating factor 1 receptor precursor | Myeloid malignancy, predisposition to | macrophage colony stimulating factor receptor activity; ATP binding; transferase activity | c-fms oncogene; fms oncogene; glycoprotein; membrane protein; proto-oncogene; signal peptide |
| 5 | NM_006186 | 2.06 | nuclear receptor subfamily 4, group A, member 2 | nuclear receptor subfamily 4, group A, member 2 isoform a; nuclear receptor subfamily 4, group A, member 2 isoform b; nuclear receptor subfamily 4, group A, member 2 isoform c; nuclear receptor subfamily 4, group A, member 2 isoform d | Parkinson disease | steroid hormone receptor activity; transcription factor activity | |
| 6 | NM_002000 | 1.871 | Fc fragment of IgA, receptor for | Fc alpha receptor isoform a precursor; Fc alpha receptor isoform b precursor; Fc alpha receptor isoform c precursor; Fc alpha receptor isoform d; Fc alpha receptor isoform e; Fc alpha receptor isoform f; Fc alpha receptor isoform g; Fc alpha receptor isof | | receptor activity; receptor signaling protein activity | |
| 7 | NM_003199 | 1.621 | transcription factor 4 | transcription factor 4 isoform b | | RNA polymerase II transcription factor activity; DNA binding | |
| 8 | NM_001733 | 1.543 | complement component 1, r subcomponent | complement component 1, r subcomponent | C1r/C1s deficiency, combined | complement component C1r activity; trypsin activity; calcium ion binding; chymotrypsin activity; hydrolase activity | |
| 9 | NM_002983 | 1.542 | chemokine (C-C motif) ligand 3 | chemokine (C-C motif) ligand 3 | | chemokine activity; antiviral response protein activity; signal transducer activity | |

TABLE 2-continued

Immune system gene regulated by the HPLC-purified peptide

| | Gene Name | TDP | Description | Product | Phenotype | function | Keywords |
|---|---|---|---|---|---|---|---|
| 10 | NM_002969 | 1.53 | mitogen-activated protein kinase 12 | mitogen-activated protein kinase 12 | | MAP kinase activity; ATP binding; protein serine/threonine kinase activity; transferase activity; SAP kinase 3 activity | |
| 11 | NM_000173 | 1.529 | glycoprotein Ib (platelet), alpha polypeptide | platelet glycoprotein Ib alpha polypeptide precursor | Bernard-Soulier syndrome | thrombin receptor activity; cell adhesion molecule activity | |
| 12 | D10202 | 1.506 | platelet-activating factor receptor | platelet-activating factor receptor | | platelet activating factor receptor activity | G-protein coupled receptor; PAF receptor; platelet-activating factor receptor |

Immune system gene suppressed by the peptide

| | Gene Name | TDP | Description | Product | Phenotype | function | Keywords |
|---|---|---|---|---|---|---|---|
| 1 | NM_006864 | 0.662 | leukocyte immunoglobulin-like receptor, subfamily B (with TM and ITIM domains), member 3 | leukocyte immunoglobulin-like receptor, subfamily B (with TM and ITIM domains), member 3 | | receptor activity | |
| 2 | NM_007052 | 0.662 | NADPH oxidase 1 | NADPH oxidase 1 isoform long; NADPH oxidase 1 isoform short; NADPH oxidase 1 isoform long variant | | superoxide-generating NADPH oxidase activity; oxidoreductase activity; voltage-gated proton channel activity | |
| 3 | NM_002258 | 0.653 | killer cell lectin-like receptor subfamily B, member 1 | killer cell lectin-like receptor subfamily B, member 1 | | sugar binding; transmembrane receptor activity | |
| 4 | NM_001776 | 0.646 | ectonucleoside triphosphate diphosphohydrolase 1 | ectonucleoside triphosphate diphosphohydrolase 1 | | apyrase activity; magnesium ion binding; hydrolase activity | |
| 5 | NM_016523 | 0.644 | killer cell lectin-like receptor subfamily F, member 1 | killer cell lectin-like receptor subfamily F, member 1 | | transmembrane receptor activity | |
| 6 | NM_014442 | 0.641 | sialic acid binding Ig-like lectin 8 | sialic acid binding Ig-like lectin 8 | | sugar binding; transmembrane receptor activity; cell adhesion molecule activity | |
| 7 | NM_004133 | 0.635 | hepatocyte nuclear factor 4, gamma | hepatocyte nuclear factor 4, gamma | | steroid hormone receptor activity; steroid binding; transcription factor activity | |
| 8 | NM_002121 | 0.633 | major histocompatibility complex, class II, DP | major histocompatibility complex, class II, | Beryllium disease, chronic, | class II major histocompatibility complex | |

TABLE 2-continued

Immune system gene regulated by the HPLC-purified peptide

| | Gene Name | TDP | Description | Product | Phenotype | function | Keywords |
|---|---|---|---|---|---|---|---|
| | | | beta 1 | DP beta 1 precursor | susceptibility to | antigen | |
| 9 | NM_000397 | 0.631 | cytochrome b-245, beta polypeptide (chronic granulomatous disease) | cytochrome b-245, beta polypeptide (chronic granulomatous disease) | Chronic granulomatous disease, X-linked | voltage-gated ion channel activity; electron transporter activity; oxidoreductase activity | |
| 10 | NM_004750 | 0.626 | cytokine receptor-like factor 1 | cytokine receptor-like factor 1 | Cold-induced sweating syndrome | receptor activity | |
| 11 | NM_003891 | 0.618 | protein Z, vitamin K-dependent plasma glycoprotein | protein Z, vitamin K-dependent plasma glycoprotein | | trypsin activity; protein binding; calcium ion binding; chymotrypsin activity | |
| 12 | NM_002260 | 0.603 | killer cell lectin-like receptor subfamily C, member 2 | killer cell lectin-like receptor subfamily C, member 2 | | sugar binding; transmembrane receptor activity | |
| 13 | NM_005545 | 0.579 | immunoglobulin superfamily containing leucine-rich repeat | immunoglobulin superfamily containing leucine-rich repeat | | protein binding | |
| 14 | NM_001311 | 0.561 | cysteine-rich protein 1 (intestinal) | cysteine-rich protein 1 (intestinal) | | zinc ion binding | |
| 15 | NM_004528 | 0.561 | microsomal glutathione S-transferase 3 | microsomal glutathione S-transferase 3 | | peroxidase activity; glutathione transferase activity | |
| 16 | NM_018661 | 0.528 | defensin, beta 103 | defensin, beta 103, precursor | | antimicrobial peptide activity; Gram-positive antibacterial peptide activity | |
| 17 | NM_002124 | 0.502 | major histocompatibility complex, class II, DR beta 1 | major histocompatibility complex, class II, DR beta 1 precursor | Pemphigoid, susceptibility to | MHC class II receptor activity | |
| 18 | Y00815 | 0.475 | protein tyrosine phosphatase, receptor type, F | protein tyrosine phosphatase, receptor type, F isoform 1 precursor; protein tyrosine phosphatase, receptor type, F isoform 2 precursor | | | antigen; cell surface glycoprotein; glycoprotein; immunoglobulin superfamily; LAR gene; leukocyte common antigen; neural cell adhesion molecule; transmembrane protein |
| 19 | NM_004636 | 0.459 | sema domain, immunoglobulin domain (Ig), short basic domain, secreted, (semaphorin) 3B | sema domain, immunoglobulin domain (Ig), short basic domain, secreted, (semaphorin) 3B | | | |
| 20 | NM_001783 | 0.4 | CD79A antigen (immunoglobulin-associated alpha) | CD79A antigen isoform 1 precursor; CD79A | | transmembrane receptor activity | |

TABLE 2-continued

Immune system gene regulated by the HPLC-purified peptide

| | Gene Name | TDP | Description | Product | Phenotype | function | Keywords |
|---|---|---|---|---|---|---|---|
| 21 | NM_004106 | 0.382 | Fc fragment of IgE, high affinity I, receptor for; gamma polypeptide | antigen isoform 2 precursor Fc fragment of IgE, high affinity I, receptor for; gamma polypeptide precursor | | receptor signaling protein activity; transmembrane receptor activity; IgE binding | |
| 22 | U77604 | 0.349 | microsomal glutathione S-transferase 2 | microsomal glutathione S-transferase 2 | | glutathione transferase activity; enzyme activator activity | |
| 23 | NM_002118 | 0.335 | major histocompatibility complex, class II, DM beta | major histocompatibility complex, class II, DM beta precursor | | chaperone activity; MHC class II receptor activity | |
| 24 | NM_002123 | 0.328 | major histocompatibility complex, class II, DQ beta 1 | major histocompatibility complex, class II, DQ beta 1 precursor | Creutzfeldt-Jakob disease, variant, resistance to | | |
| 25 | K01171 | 0.319 | major histocompatibility complex, class II, DR alpha | major histocompatibility complex, class II, DR alpha precursor | | MHC class II receptor activity | antigen; class II antigen; histocompatibility antigen; major histocompatibility complex |
| 26 | NM_006120 | 0.298 | major histocompatibility complex, class II, DM alpha | major histocompatibility complex, class II, DM alpha precursor | | | |

The present inventor has verified the validity of this diagnosis method using 55000 cancer-related genes. When such a great number of cancer-related genes are used, DNA chip technology is preferably used. In the DNA chip technology, each DNA of the cancer-related genes is immobilized so as to be arrayed on a slide; the above-mentioned labeled cRNA solution is dropped into the slide; the cRNA which is not hybridized is removed by washing; and fluorescence intensity of each gene position is detected by a scanner. The results are compared with the result which is obtained by conducting the same process using the above-mentioned control solution. Thus, cancer-related genes of which expression is increased or decreased when cells or tissues are treated with the peptide of the present invention can be exhaustively analyzed.

Therefore, a combination of such a cancer-related gene, the peptide of the present invention, and a polynucleotide encoding the peptide is useful as a cancer diagnostic reagent kit for determining a tendency of canceration or malignancy of cancer.

[Diagnosis Method 3]

The peptide of the present invention is also used as an antigen for preparing a specific antibody against the peptide. The specific antibody is useful as a diagnostic reagent. The antibody may be either polyclonal or monoclonal antibody, and these antibodies can be prepared by known methods. For example, the polyclonal antibody can be prepared as an antiserum by immunizing an animal such as mouse, rat, or rabbit with the peptide of the present invention. The antiserum may be further purified. The monoclonal antibody can be prepared by a hybridoma method: extracting spleen cells from the above-mentioned sensitized animal and fusing the spleen cells with myeloma cells to form hybridomas.

In the immunization, an appropriate adjuvant may be used. In addition, the peptide of the present invention may be used as a conjugate with a carrier protein such as keyhole limpet hemocyanin for increasing the immunogenicity of the peptide.

The antibody against the peptide of the present invention is used as a diagnostic reagent for determining malignancy of cancer, wherein a specimen, such as cancer tissues or cells, is stained by using the specific antibody labeled with an appropriate fluorescence dye or the like. When the peptide of the present invention is detected in the tissues or cells, it is suggested that cancer is advancing. The amount of the peptide can be determined by measuring the fluorescence intensity. A large amount of the peptide indicates that the malignancy of cancer is considerably high.

Additionally, the antibody against the peptide of the present invention can be used as a diagnostic reagent for measuring a tendency of canceration (easiness of conversion to cancer: a degree of risk of canceration). In such a use of the antibody, a specimen of the tissues or cells shown in diagnosis methods 1 and 2 is stained using the labeled antibody. When the peptide of the present invention is detected in these tissues or cells, it is suggested that the tissues or cells are exposed to cancer-inducing stress, i.e., a degree of risk of canceration is high. When the amount of the peptide of the present invention is large, it is suggested that the tendency is further higher. When the specimen is cancer cells, a large amount of the peptide suggests that the malignancy of the cancer is high.

Furthermore, the antibody against the peptide of the present invention can be expected to have an anticancer effect such as suppression of cancer cell proliferation as a cancer-cell proliferation-suppressing drug. In addition, the antibody can be expected to block malignant alteration or mutation acceleration to which normal cells are subjected as a cancer-preventing drug. Furthermore, by binding the antibody to an anticancer agent, a drug which may be used for missile therapy can be obtained.

EXAMPLES

Examples of the present invention will now be described, but the present invention is not limited to these examples.

Example 1

Preparation and Sequencing of the Peptide of the Present Invention (Cell: UTC-8)

The squamous-cell carcinoma cell (UTC-8: FERM BP-08611) is a highly differentiated type with high metastasis potential and keratinization tendency. The cell also has high adhesion and proliferation ability and becomes confluent in 5 to 7 days after inoculating $1 \times 10^5$ cells into a culture medium (5 ml) in a T25 culture flask (Falcon).

(Cell-Culturing Condition)

The following processes were performed: inoculating $1 \times 10^6$ UTC-8 cells into 10 T150 culture flasks (Falcon); performing initial culture in 20 ml RPMI1640 culture medium with 10% FCS (GIBCO); and additionally supplying 30 ml of the culture medium when the proliferation reached about 30% of the culture flask dimension. The culture was performed in 5% $CO_2$ and 95% humidity at an incubator internal temperature of 37° C. When the cells become 80% confluent (the proliferation of the cells is maintained at the point just before the cell proliferation reaches its peak), the antigen peptide bound to HLA was eluted from the cell membrane surfaces.

(Antigen Peptide-Eluting Procedure)

The culture medium for the UTC-8 cells was removed when the cells became 80% confluent in each T150 culture flask (Falcon). The cells were washed with Hanks solution once and then with 30 ml of a PBS solution not containing divalent calcium ion and divalent magnesium ion twice. Then, after the sufficient removal of the solution, 10 ml of a citrate-phosphate buffer having a pH of 3.3 to 3.4 was added to each flask, and the cells were left at a room temperature for 2 min.

Then, the citrate-phosphate buffer solution was collected and centrifuged at 1200 rpm for 7 min, and the supernatant was filtered through a 0.45 µm filter (Millex-HV PVDF: MILLIPORE). The filtrate was further filtered through a 0.22 µm filter. The filtrate was desalted with Sep-Pac C18 cartridge (Waters), and the target substance bound to the cartridge was eluted with a 60% (v/v) acetonitrile aqueous solution as a crude extract solution. The thus obtained crude extract solution was frozen and stored at −20° C. for later HPLC.

The cells received the above-described treatment were washed, immediately after the collection with the citrate-phosphate buffer solution having a pH of 3.3 to 3.4, with 30 ml of Hanks solution twice. Then, the cells were recultured in 30 ml of RPMI 164 medium containing 10% FCS. This treatment was subjected to the same cells once a day for successive 4 days.

(Lyophilization and Redissolution of Crude Extraction)

The crude extract solution obtained in above was lyophilized using a lyophilizer (FD-1000: EYELA) under conditions at a trapping temperature of −40° C. and at a degree of vacuum of 15 Pa or less. The dried sample was redissolved in 5 ml of the citrate-phosphate buffer solution having a pH of 3.3 to 3.4. At this stage, the total protein amount determined by Lowry method was 400 µg.

(Two-Dimensional Electrophoresis)

Ten micrograms of the thus obtained molecule was applied to two-dimensional electrophoresis, but no band was visible to the naked eye by Coomassie Brilliant Blue (CBB) R250 staining (detection sensitivity: 1 µg) and also by silver staining having a sensitivity as high as about 1000 times that of the CBB staining, (theoretical sensitivity: 1 ng, actual sensitivity: about 20 times that of the CBB staining). This suggests that the peptide molecule physically passes through a gel (silica gel C18) generally used in the two-dimensional electrophoresis. This is an unusual characteristic of the peptide molecule of the present invention.

(Fractionating by Gel Filtration)

Since the molecule of the present invention cannot be detected by usual two-dimensional electrophoresis, it was tried to detect the molecule by an HPLC system. The target peptide was obtained as a fraction obtained by using an AKTA Explorer 10 (Amersham Pharmacia Biotech) HPLC system and Superdex Peptide 10/300 GL (Amersham Pharmacia Biotech) as a gel-filtration column; using a citrate-phosphate buffer solution (0.1 M citric acid and 0.2 M phosphoric acid) having a pH of 6.8 as an elution buffer at a flow rate of 0.2 ml/min; and isolating a peak in a fraction at an elution volume of 20.8 to 22.8 ml by using a detection wavelength of 214 nm. The obtained fraction was lyophilized and then redissolved in sterilized redistilled water for desalting. The desalting was performed by fractionating by the AKTA Explorer 10 (Amersham Pharmacia Biotech) HPLC system and Superdex Peptide 10/300 GL (Amersham Pharmacia Biotech) as a gel-filtration column using distilled water as a solvent at a flow rate of 0.2 ml/min. The target peptide was obtained as a fraction at an elution volume of 11.4 to 20.0 ml.

FIG. 1 shows an elution profile of the gel filtration.

The peptide was lyophilized using the lyophilizer FD-1000 (EYELA) and stored at −20° C. for later mass spectrometry.

(Optimal pH)

The optimal pH of the elution buffer was 6.8 to 7.2. When the pH of the elution buffer was 7.3 or more, peaks were further divided into smaller peaks. When the pH of the elution buffer was 6.7 or less, peaks, which were isolated from each other at a pH of 6.8, lapped over each other, and the gel filtration resolution was decreased.

(Detection Wavelength)

The peptide is characterized by the fact that the peak of the peptide in the crude extract solution can be separately detected by using physiological activity as an indicator only when a detection wavelength of 214 nm is used. However, the peptide cannot be detected when a detection wavelength of 254 to 257 nm or of 280 nm, which are generally used in peptide detection, is used. These results suggest that the amino acid composition of the peptide has extremely low contents of tyrosine (absorption wavelength: 280 nm), tryptophan (absorption wavelength: 280 nm), and phenylalanine (absorption wavelength: 257 nm); or that the peptide does not substantially contain such amino acids. The use of a detection wavelength of 214 nm has a demerit such that many interfering substances are also detected by ultraviolet absorption spectrometry. However, it can precisely measure a protein amount (quantitative detection range: 5 to 1000 μg) regardless of types of proteins. The 214 nm is the most appropriate wavelength for, as in this experiment, precisely measuring a concentration of unknown peptide in a crude extract solution by detecting a peak utilizing peptide-bond absorption without denaturation of the peptide to maintain the physiological activity. On the other hand, the quantitative detection property was further improved by using a detection wavelength of 205 nm when the crude extract solution containing the peptide was applied to a desalting column (Sep-Pack 18) or to a molecular sieve (Centricon YM-3) for removing foreign substances such as nucleic acids as far as possible, by intending only purification of the peptide without any concern for maintaining the physiological activity. Therefore, when a peak in the crude extract solution was detected using the physiological activity as an indicator, a detection wavelength of 214 nm was used, and when the precise quantitative determination was necessary, a detection wavelength of 205 nm was used.

(Fractionating Flow Rate in Column)

The fractionating flow rate is important for separating the peptide. Namely, the flow rate of an elution buffer is determined so that molecules slowly pass through the column to effectively utilize advantages of the molecular sieve. When the flow rate was 0.28 ml/min, adjacent peaks lapped over each other; thus, the separation resolution was insufficient. For the detection of the peak of the present invention, a low flow rate of 0.14 ml/min was optimal. Each fraction was determined to be 0.1 ml/well from the view point of the width of the peak, and was collected in a 96-well plate (Nunc).

(Structure Analysis of the Peptide by Mass Spectrometer)

The peptide fraction that was stored after lyophilization was redissolved in sterilized redistilled water, and 5 μg as a protein was separated by ProteinChip Series 4000 system (Cipergen). The sample (5 μg) was bound to the ProteinChip by using MilliQ water as a binding/wash buffer in normal-phase ProteinChip and using 100 mM sodium acetate (pH 4.0) as a binding/wash buffer in cation exchange ProteinChip, and was measured by using alpha-cyano-4-hydroxy-cinnamic acid (CHCA) as an energy-absorbing molecular in a mass range of 800 to 2500 m/z. As a result, a peak of a molecular weight which was thought to be that of the target peptide was detected. By using the detection conditions clarified by the above-described processes as a reference, the target peptide trapped on the chip was analyzed by a mass spectrometer, QSTAR XL LC/MC/MS system (Applied Biosystems). Then, on the basis of the results of time-of-flight (TOF mass spectrometry) analysis of the fragmented peptide-constituting portion, a data base (Mascot Search Results: Matrix Science) was searched for a sequence of the peptide to reveal that the peptide had the following peptide sequence of which function was unknown as of Jan. 27, 2005.

```
Peptide:
                                        (SEQ ID NO: 1)
Gln-Pro-Gln-Phe-Gly-Arg-Arg-Met-Glu-Ser-Lys
```

Example 2

Confirmation of Expression of the Peptide of the Present Invention in Original Cancer Cell UTC-8

The fact that the peptide obtained in Example 1 was actually expressed in the original cancer cell UTC-8 at a gene level was confirmed as follows:

UTC-8 cells after the extraction of the peptide of the present invention were recultured, and total RNA was extracted from the recultured UTC-8 cells after 2 hr, 4 hr, and 6 hr from the extraction, respectively, by using an RNA extraction kit (QIAGEN). Then, cDNA was synthesized using each of the extracted total RNA as a template to produce a cDNA pool. On the basis of the amino acid sequence (SEQ ID NO: 1) of the peptide, the following primers were designed. Fw primers (DNAs encoding four contiguous amino acids of the peptide were synthesized so that the N-terminal of the four contiguous amino acids shifted one by one from the N-terminal of the peptide toward the C-terminal.)

```
MHC 1-4      CAR CCN CAR TTY        (SEQ ID NO: 2)

MHC 2-5      CCN CAR TTY GGN        (SEQ ID NO: 3)

MHC 3-6      CAR TTY GGN AGR        (SEQ ID NO: 4)

MHC 4-7      TTY GGN AGR AGR        (SEQ ID NO: 5)

MHC 5-8      GGN AGR AGR ATG        (SEQ ID NO: 6)

MHC 6-9      AGR AGR ATG GAR        (SEQ ID NO: 7)

MHC 7-10     AGR ATG GAR TCN        (SEQ ID NO: 8)

MHC 8-11     ATG GAR TCN AAR        (SEQ ID NO: 9)

(N: A, T, C, or G, R: G or A, Y: C or T)
Rv primer (a gene sequence produced for an
amino acid sequence at the C-terminal of the
peptide): Oligo-dT primer (poly-A primer)
```

Here, the poly-A primer was used as the Rv primer in order to obtain cDNA synthesized from mRNA.

Complementary DNAs were synthesized by reverse transcription from total RNA which was extracted at each time to produce a cDNA pool. Then, PCR was performed using this cDNA pool as templates and using primers synthesized as described above under conditions at 94° C. for 3 min, at 55° C. for 1 min, and at 74° C. for 1 min as one cycle. The cycle was repeated 35 cycles in total. After agarose-gel electrophoresis, 12 bands were selected from a sample of which RNA was extracted after 4 hr when the signal intensity was largest. The size of each band was about 500 to 2000 bp. Genes of these bands extracted from the gel were inserted into pGM easy vectors.

Insert of the genes into 12 types of the pGM easy vectors was checked, and 8 samples per one type of the vector were sequenced. As a result, it was confirmed that all the sequences of the 8 samples included a common sequence shown in Table 3 below, though the DNA lengths of the sequences were different from those of each other.

TABLE 3

```
                            10         20
MHClike001   Sequence   -CAGCCCCAG TTTGGTAGGA GGATGGAGTC TAAGACT--- ---------- ----AAGG-- (SEQ ID NO: 10)
                            80         90
MHClike002   Sequence   TCAGCCGCAG TTTGGTAGAA GGATGAGTTC CAAGCTGATA CAAACCTGCA CCCTTCTCAG (SEQ ID NO: 11)
                            80         90
MHClike003   Sequence   TCACTCAAAG G-CGGTAATA CGGTTATCCA CAGAATC--- -AGGGGATAA CGCAGGAAAG (SEQ ID NO: 12)
                           160        170
MHClike004-a Sequence   TCAGCCTCAG TTTGGTAGAA GGATGGAGTC GAAGATC--- --AAGGCAAT GGC-AGGA-- (SEQ ID NO: 13)
                            80         80
MHClike004-b Sequence   TCAGCCTCAA TTTGGGAGGA GGATGGAATC CAAGCTGCCA GAACTTCTGA CCTGAGTGGG (SEQ ID NO: 14)
                            10         20
MHClike005-a Sequence   -CAGCCACAA TTTGGTAGGA GGATGGAGTC CAAGTGACCG AAGAGCAAGG CTGTCCAAGC (SEQ ID NO: 15)
                            10         20
MHClike005-b Sequence   -CAGCCTCAG TTCGGGAGGA GGATGGAGTC AAAGAATAA- GTGGACGCCG GCTGGGTTCA (SEQ ID NO: 16)
                            10         20
MHClike006   Sequence   -CAGCCGCAG TTTGGGAGGA GGTAGAGGGT GGGGTGGCGG GTGCAGACTC CTCCGCTGAG (SEQ ID NO: 17)
```

The result shows the fact that a gene being common in or complementary to the gene encoding the peptide of the present invention is surely present in original cancer cell UTC-8 and that the peptide is derived from UTC-8 cells.

Example 3

Artificial Synthesis of the Peptide of the Present Invention by Fmoc Method The peptide was artificially synthesized by an in vitro synthesis system (Abacus: Sigma Genosys).

The peptide was synthesized using an activated cellulose membrane (SPOTs: Sigma Genosys) as follows: The α-amino groups of amino acids were protected with 9-fluorenyl methoxy carbonyl (Fmoc) and the carboxyl groups were protected with an active ester (Opfp or Odhbt). These amino acid derivatives were dissolved in 1-methyl-2-pyrrolidinone (NMP). About 1 µl of the amino acid derivative solution (equivalent to 100 to 200 µg of Fmoc-amino acid) was spotted on the membrane at each marked position where a spacer arm was bound thereto. The end of the spacer arm had a free amino group, and the spots were colored to blue with bromophenol blue (BPB). An amido bond was formed by the reaction between the amino group on the membrane and the active ester. Then, capping was carried out as follows: Excess amino acid derivatives were rinsed away with dimethylformamide (DMF), and then unreacted amino group was acetylated by treating with acetic anhydride/DMF so as to be lost the reactivity. Then, the Fmoc group protecting the amino group was removed by secondary amine, piperidine/DMF, in order to let the amino group free for the subsequent extension reaction. Additionally, after all synthesis processes were completed, deprotection of the side chains was carried out. Namely, a t-butyl alcohol-based protecting group (Pmc, OtBu, Trt, tBoc, tBu, etc.) protecting the reactive side chains was removed by using trifluoroacetate (TFA) mixed with dichloromethane (DCM)/triisobutylsilane. Thus, the target peptide was artificially synthesized.

Example 4

Influence of the Artificially Synthesized Peptide on Normal Cell Gene (a) The peptide obtained in Example 3 was added to a human normal peripheral blood monocyte culture system (10 to 100 µg peptide/$1\times10^6$ to $1\times10^7$ monocytes), and they were cocultured for 7 hr. Then, mRNA was extracted from the monocytes and was applied to analysis for up-regulation and down-regulation in respect to about 55000 human genes by using DNA chip system (Clontech). Table 4 shows a part of the genes.

TABLE 4

| | | | | A. Enhanced Gene | | | |
|---|---|---|---|---|---|---|---|
| Gene No. | Gene Name | Gene Bank | | Expression Amount before Treatment with the Peptide | Expression Amount after Treatment with the Peptide | Enhancement Ratio | Description |
| 1. Oncogene | | | | | | | |
| 1 | 21713 | NM_004339.2 | GE480864 DISCOVERY | 0.168670654 | 7.741943359 | 45.89976479 | zn87b11y5 Stratagene lung carcinoma 937218 cDNA clone IMAGE: 565149 5' similar to contains Alu repetitive element; |

TABLE 4-continued

| | | | | | | | | |
|---|---|---|---|---|---|---|---|---|
| | 2 | 32050 | CB999164.1 | GE540894 | DISCOVERY | 0.344818115 | 9.805541992 | 28.43685282 | contains element MER22 repetitive element; disrupted in renal carcinoma 1 (DIRC1) |
| | 3 | 34854 | NM_198502.1 | GE603511 | DISCOVERY | 0.040802002 | 1.098205566 | 26.91548242 | *Homo sapiens* NEUROBLASTOMA COT 25-NORMALIZED cDNA clone CS0DC018YE24 3-PRIME |
| | 4 | 46997 | AL831827.1 | GE547122 | DISCOVERY | 11.17044067 | 236.1818237 | 21.14346521 | clone N11 NTera2D1 teratocarcinoma mRNA |
| | 5 | 37781 | AI478531.1 | GE645872 | DISCOVERY | 2.533325195 | 32.40939331 | 12.79322267 | NEUROBLASTOMA COT 25-NORMALIZED cDNA clone CS0DC011YD03 5-PRIME |
| | 6 | 7394 | AA021565.1 | GE707587 | DISCOVERY | 29.597229 | 350.270813 | 11.8345813 | HELA CELLS COT 25-NORMALIZED cDNA clone CS0DK007YM05 3-PRIME |
| | 7 | 22388 | CD244420.1 | GE692174 | DISCOVERY | 60.32098389 | 571.2325439 | 9.469881078 | zb91f05s1 Soares_parathyroid_tumor_ NbHPA cDNA clone IMAGE: 320193 3' |
| | 8 | 6231 | BF973345.1 | GE54360 | DISCOVERY | 0.583343506 | 5.453491211 | 9.348679048 | breast carcinoma amplified sequence 1 (BCAS1) |
| | 9 | 34979 | BC041456.1 | GE631189 | DISCOVERY | 2.651672363 | 24.171875 | 9.115709518 | yu38e06r1 Soares ovary tumor NbHOT cDNA clone IMAGE: 236098 5' |
| | 10 | 4210 | NM_152577.1 | GE493259 | DISCOVERY | 61.90475464 | 393.7416382 | 6.360442594 | RAS-like, family 11, member A (RASL11A) |
| | 11 | 36631 | AW302705.1 | GE53805 | DISCOVERY | 71.11248779 | 417.5 | 5.87098009 | RAB43, member RAS oncogene family (RAB43), mRNA |
| | 12 | 29317 | AA601191.1 | GE551636 | DISCOVERY | 2.891571045 | 10.05682373 | 3.477979124 | T-cell leukemia/lymphoma 6 (TCL6), transcript variant TCL6a1 |
| | 13 | 14195 | NM_002170.2 | GE55306 | DISCOVERY | 2.811950684 | 7.21875 | 2.567168067 | B-cell translocation gene 4 (BTG4) |
| | 14 | 2183 | AA861218.1 | GE80525 | DISCOVERY | 3.408691406 | 8.622650146 | 2.529607148 | neuro-oncological ventral antigen 1 (NOVA1), transcript variant 1 |
| | 15 | 22675 | BX117842.1 | GE516913 | DISCOVERY | 81.83721924 | 204.4117737 | 2.497784939 | endogenous retroviral family W, env(C7), member 1 (syncytin) (ERVWE1), mRNA |
| | 16 | 3858 | AI283196.1 | GE59314 | DISCOVERY | 9.184204102 | 22.61538696 | 2.46242208 | preferentially expressed antigen in melanoma (PRAME), transcript variant 3 |
| | 17 | 8431 | NM_021081.3 | GE56485 | DISCOVERY | 7.641021729 | 18.609375 | 2.435456365 | Ras-associated protein Rap1 (RBJ) |
| | 18 | 18829 | NM_002958.1 | GE81500 | DISCOVERY | 6.883331299 | 15.3157959 | 2.225055752 | v-myc myelocytomatosis viral related oncogene, neuroblastoma derived (avian) (MYCN) |
| | 19 | 8440 | NM_016232.4 | GE79419 | DISCOVERY | 7.225799561 | 15.71429443 | 2.174748179 | mab-21-like 2 (*C elegans*) (MAB21L2) |
| | 20 | 3642 | AW594132.1 | GE543964 | DISCOVERY | 1627.052002 | 3306.942871 | 2.032475217 | RAB2, member RAS oncogene family (RAB2) |
| | 21 | 38566 | NM_031273.1 | GE84875 | DISCOVERY | 7.339630127 | 14.54998779 | 1.982387061 | RAS protein activator like 2, mRNA (cDNA clone IMAGE: 5399841), with apparent retained intron |
| | 22 | 24910 | NM_018556.2 | GE60436 | DISCOVERY | 29.01333618 | 55.05334473 | 1.897518589 | platelet-derived growth factor beta polypeptide (simian sarcoma viral (v-sis) oncogene homolog) (PDGFB), transcript variant 2 |
| | 23 | 6329 | BX116538.1 | GE58014 | DISCOVERY | 37.80822754 | 67.53659058 | 1.786293486 | mutated in colorectal cancers (MCC) |
| 2. Immune System Gene | | | | | | | | | |
| | 1 | 25767 | INCYTE UNIQUE | GE59636 | DISCOVERY | 130.6451721 | 4927.383301 | 37.71577029 | tumor necrosis factor (TNF superfamily, member 2) (TNF) |
| | 2 | 29703 | BX103139.1 | GE59980 | DISCOVERY | 0.660003662 | 19.8302002 | 30.04559116 | chemokine (C—X—C motif) ligand 9 (CXCL9) |

TABLE 4-continued

| | | | | | | | |
|---|---|---|---|---|---|---|---|
| 3 | 28615 | AA504638.1 | GE520093 | DISCOVERY | 2.739135742 | 20.69332886 | 7.554692722 IL3-UT0117-080301-496-D07 UT0117 *Homo sapiens* cDNA |
| 4 | 30707 | AI809890.1 | GE54001 | DISCOVERY | 2.853668213 | 21.05661011 | 7.378787069 immunoglobulin superfamily, member 4C (IGSF4C) |
| 5 | 21607 | NM_002960.1 | GE80951 | DISCOVERY | 3.446289063 | 24.92727661 | 7.233077713 colony stimulating factor 1 (macrophage) (CSF1), transcript variant 1 |
| 6 | 51904 | H08511.1 | GE893705 | DISCOVERY | 2.304870605 | 11.3684082 | 4.932341181 interleukin 1 family, member 8 (eta) (IL1F8), transcript variant 1 |
| 7 | 22254 | NM_176891.2 | GE80659 | DISCOVERY | 26.98571777 | 122.6947327 | 4.546654408 interleukin 4 (IL4), transcript variant 1 |
| 8 | 45170 | BM671892.1 | GE53155 | DISCOVERY | 38.31506348 | 85.25881958 | 2.225203663 transforming growth factor beta 1 induced transcript 1 (TGFB1I1) |
| 9 | 22100 | BX457477.2 | GE616415 | DISCOVERY | 328.440918 | 608.4909058 | 1.852664734 IL5-CI0001-181000-178-f03 CI0001 *Homo sapiens* cDNA |

B. Suppressed Gene

| Gene No. | Gene Name | Gene Bank | | Expression Amount before Treatment with the Peptide | Expression Amount after Treatment with the Peptide | Suppression Ratio | Description |
|---|---|---|---|---|---|---|---|
| 1. Cancer Suppressing Gene | | | | | | | |
| 1 | 35687 | BX108016.1 | GE82100 | DISCOVERY | 103.9224243 | 0.225219727 | 461.4268293 heat shock protein 75 (TRAP1) |
| 2 | 36334 | BF433017.1 | GE82101 | DISCOVERY | 341.440918 | 2.079650879 | 164.1818449 heat shock 70 kDa protein 14 (HSPA14) |
| 3 | 37600 | AW979088.1 | GE62125 | DISCOVERY | 982.9432373 | 8.42855835 | 116.6205651 AHA1, activator of heat shock 90 kDa protein ATPase homolog 1 (yeast) (AHSA1) |
| 4 | 30909 | NM_018412.2 | GE79080 | DISCOVERY | 987.7108154 | 11.47369385 | 86.08481528 tumor rejection antigen (gp96) 1 (TRA1) |
| 5 | 8280 | BC063301.1 | GE62103 | DISCOVERY | 758.4154053 | 9 | 84.26837836 brain specific protein (CGI-38) |
| 6 | 11438 | NM_152271.2 | GE82058 | DISCOVERY | 1207.091431 | 14.74417114 | 81.86905991 serologically defined breast cancer antigen 84 (SDBCAG84), transcript variant 1 |
| 7 | 11261 | NM_018559.2 | GE56225 | DISCOVERY | 379.1338501 | 6.257141113 | 60.59218471 breast cancer metastasis suppressor 1 (BRMS1) |
| 8 | 50395 | NM_004480.3 | GE79552 | DISCOVERY | 470.2086792 | 8.763153076 | 53.65747638 Ras suppressor protein 1 (RSU1), transcript variant 1 |
| 9 | 52111 | AK056875.1 | GE61359 | DISCOVERY | 593.6870728 | 13.6000061 | 43.65344164 leukemia cell normalized cDNA library cDNA clone LEU1757_26_C2 |
| 2. Immune System Gene | | | | | | | |
| 1 | 20881 | NM_001482.1 | GE61110 | DISCOVERY | 6599.050293 | 38.16882324 | 172.891112 natural killer cell transcript 4 (NK4) |
| 2 | 47973 | NM_004394.1 | GE81458 | DISCOVERY | 1480.68396 | 9.638885498 | 153.615681 CD8 antigen, beta polypeptide 1 (p37) (CD8B1), transcript variant 5 |
| 3 | 10791 | W00901.1 | GE80378 | DISCOVERY | 517.4453125 | 3.42855835 | 150.9221252 HLA-B associated transcript 5 (BAT5) |
| 4 | 15907 | BU899259.1 | GE80960 | DISCOVERY | 912.8641357 | 6.363647461 | 143.4498283 intercellular adhesion molecule 2 (ICAM2) |
| 5 | 16756 | AI707455.1 | GE81522 | DISCOVERY | 395.0359497 | 2.80645752 | 140.7596399 major histocompatibility complex, class I, E (HLA-E) |
| 6 | 34736 | AV736303.1 | GE80100 | DISCOVERY | 3974.221191 | 29.0786438 | 136.6714768 adhesion molecule AMICA (AMICA) |
| 7 | 39991 | AI252940.1 | GE61199 | DISCOVERY | 2414.748779 | 17.77420044 | 135.8569567 lymphotoxin beta (TNF superfamily, member 3) (LTB), transcript variant 2 |
| 8 | 41726 | AI453596.1 | GE58507 | DISCOVERY | 4512.05127 | 33.50683594 | 134.660619 apoptosis-associated speck-like protein containing a |

TABLE 4-continued

| | | | | | | | |
|---|---|---|---|---|---|---|---|
| | | | | | | | CARD (ASC), transcript variant 1 |
| 9 | 45767 | BG190549.1 | GE79374 | DISCOVERY | 2359.263184 | 18.125 | 130.1662446 | HLA-B associated transcript 1 (BAT1), transcript variant 1 |
| 10 | 42614 | AW296107.1 | GE81744 | DISCOVERY | 626.2438965 | 4.848480225 | 129.1629268 | killer cell lectin-like receptor subfamily K, member 1 (KLRK1) |
| 11 | 20551 | AK024566.1 | GE86210 | DISCOVERY | 2811.726807 | 22.93103027 | 122.6166802 | IL2-inducible T-cell kinase (ITK) |
| 12 | 38103 | NM_173695.1 | GE61298 | DISCOVERY | 703.8875122 | 5.777770996 | 121.8268278 | tumor necrosis factor receptor superfamily, member 7 (TNFRSF7) |
| 13 | 37068 | AW971488.1 | GE58019 | DISCOVERY | 6960.161133 | 57.38461304 | 121.2896762 | immediate early response 2 (IER2) |
| 14 | 4899 | BX115183.1 | GE80961 | DISCOVERY | 536.4679565 | 4.5 | 119.2151015 | interferon (alpha, beta and omega) receptor 2 (IFNAR2), transcript variant 1 |
| 15 | 43032 | BC013284.2 | GE58028 | DISCOVERY | 519.3710938 | 4.445770264 | 116.8236465 | interferon, gamma-inducible protein 16 (IFI16) |
| 16 | 42813 | NM_001763.1 | GE58393 | DISCOVERY | 4447.713379 | 38.51351929 | 115.4844704 | granzyme A (granzyme 1, cytotoxic T-lymphocyte-associated serine esterase 3) (GZMA) |
| 17 | 22326 | NM_014396.2 | GE82907 | DISCOVERY | 1102.541626 | 9.742858887 | 113.1640763 | immune associated nucleotide 2 (hIAN2) |
| 18 | 37445 | NM_007068.2 | GE60016 | DISCOVERY | 1671.436768 | 14.875 | 112.365497 | mal, T-cell differentiation protein (MAL), transcript variant d |
| 19 | 22890 | BX119833.1 | GE86305 | DISCOVERY | 1112.63855 | 9.902160645 | 112.3632094 | NK inhibitory receptor precursor (NKIR) |
| 20 | 16478 | NM_020530.3 | GE54528 | DISCOVERY | 663.3167725 | 6.018188477 | 110.2186771 | tumor necrosis factor (ligand) superfamily, member 12 (TNFSF12), transcript variant 1, mRNA |
| 21 | 52539 | AI133415.1 | GE82473 | DISCOVERY | 17346.24609 | 158.6896667 | 109.3092351 | major histocompatibility complex, class II, DR alpha (HLA-DRA) |
| 22 | 41803 | NM_178313.1 | GE735470 | DISCOVERY | 89.23596191 | 0.820007324 | 108.8233718 | programmed cell death 2 (PDCD2), transcript variant 2 |
| 23 | 41817 | NM_016292.1 | GE79992 | DISCOVERY | 10618.77539 | 98.42697144 | 107.8848128 | major histocompatibility complex, class I, F (HLA-F) |
| 24 | 18884 | NM_015604.2 | GE57715 | DISCOVERY | 339.244873 | 3.387084961 | 100.1583595 | (clone 38-1) MHC class I mRNA fragment. |
| 25 | 8922 | NM_024077.2 | GE57504 | DISCOVERY | 10964.4248 | 110.8526306 | 98.90991981 | interferon induced transmembrane protein 1 (9-27) (IFITM1) |
| 26 | 24969 | AV752332.1 | GE60370 | DISCOVERY | 2446.138672 | 25.71212769 | 95.13559911 | CD69 antigen (p60, early T-cell activation antigen) (CD69) |
| 27 | 8634 | BC043004.2 | GE566269 | DISCOVERY | 947.6875 | 10.19564819 | 92.9501962 | perforin 1 (pore forming protein) (PRF1) |
| 28 | 38879 | NM_182832.1 | GE476899 | DISCOVERY | 2933.067871 | 31.93505859 | 91.84476247 | interferon stimulated gene 20 kDa (ISG20) |
| 29 | 49586 | BG289120.1 | GE58687 | DISCOVERY | 248.4822998 | 2.715911865 | 91.49129726 | interleukin-1 receptor-associated kinase 4 (IRAK4) |
| 30 | 11651 | AW850450.1 | GE85351 | DISCOVERY | 1144.841431 | 12.83999634 | 89.16213062 | implantation-associated protein (DKFZp564K142) |
| 31 | 53172 | NM_022749.4 | GE59644 | DISCOVERY | 577.4226074 | 6.560333252 | 88.01726761 | transforming growth factor, beta 1 (Camurati-Engelmann disease) (TGFB1) |
| 32 | 49622 | CB052158.1 | GE59962 | DISCOVERY | 3421.524414 | 39.68115234 | 86.22542976 | intercellular adhesion molecule 3 (ICAM3) |
| 33 | 22868 | NM_152285.1 | GE79323 | DISCOVERY | 539.8291016 | 6.525421143 | 82.72708991 | lymphocyte cytosolic protein 2 (SH2 domain containing leukocyte protein of 76 kDa) (LCP2) |
| 34 | 23827 | BG221408.1 | GE59882 | DISCOVERY | 2403.98877 | 29.7802124 | 80.72436613 | major histocompatibility complex, class II, DM alpha (HLA-DMA) |
| 35 | 18139 | AA938869.1 | GE890404 | DISCOVERY | 2660.284912 | 33.11999512 | 80.32262392 | major histocompatibility complex, class II, DQ alpha 1 (HLA-DQA1) |
| 36 | 22789 | BX104097.1 | GE61439 | DISCOVERY | 731.80896 | 9.725494385 | 75.24645339 | CASP8 and FADD-like apoptosis regulator (CFLAR) |
| 37 | 11236 | NM_003937.1 | GE58794 | DISCOVERY | 4738.49707 | 65.4675293 | 72.37934777 | natural killer cell group 7 sequence (NKG7), mRNA |
| 38 | 10204 | AW197778.1 | GE81039 | DISCOVERY | 696 | 9.714294434 | 71.64699451 | interferon-related developmental regulator 1 (IFRD1) |

TABLE 4-continued

| | | | | | | | | |
|---|---|---|---|---|---|---|---|---|
| 39 | 49170 | AA577911.1 | GE61247 | DISCOVERY | 713.4000244 | 10.09091187 | 70.69728028 | interferon gamma receptor 2 (interferon gamma transducer 1) (IFNGR2) |
| 40 | 42474 | AW137161.1 | GE62833 | DISCOVERY | 1164.558472 | 17.03775024 | 68.35165764 | programmed cell death 6 (PDCD6) |
| 41 | 52342 | NM_006147.2 | GE54992 | DISCOVERY | 1200.007446 | 18.71737671 | 64.11194608 | apoptosis-related protein PNAS-1 (FLJ39616) |
| 42 | 42573 | NM_022648.2 | GE79383 | DISCOVERY | 953.4078369 | 15.75 | 60.53383092 | T-cell activation protein (PGR1) |
| 43 | 24440 | NM_182936.1 | GE592149 | DISCOVERY | 14 | 0.234771729 | 59.63239308 | THYMUS cDNA clone CS0CAP007YL06 5-PRIME |
| 45 | 24440 | NM_182936.1 | GE592149 | DISCOVERY | 14 | 0.234771729 | 59.63239308 | THYMUS cDNA clone CS0CAP007YL06 5-PRIME |
| 46 | 24440 | NM_182936.1 | GE592149 | DISCOVERY | 14 | 0.234771729 | 59.63239308 | THYMUS cDNA clone CS0CAP007YL06 5-PRIME |
| 47 | 46186 | NM_032746.1 | GE82057 | DISCOVERY | 1407.181763 | 25.55319214 | 55.06872703 | cell death-regulatory protein GRIM19 (GRIM19) |
| 48 | 39926 | INCYTE UNIQUE | GE82589 | DISCOVERY | 17409.49609 | 317.7109375 | 54.79665331 | thymosin-like 6 (TMSL6) |
| 49 | 47689 | AK097380.1 | GE61992 | DISCOVERY | 3803.877441 | 72.08435059 | 52.7698094 | killer cell lectin-like receptor subfamily B, member 1 (KLRB1) |
| 50 | 12812 | CF135919.1 | GE55506 | DISCOVERY | 1176.72522 | 24.53225708 | 47.96644744 | ovarian carcinoma immunoreactive antigen (OCIA) |
| 51 | 15994 | R25284.1 | GE79364 | DISCOVERY | 11397.33301 | 239.4736938 | 47.5932568 | beta-2-microglobulin (B2M) |
| 52 | 52071 | BM698907.1 | GE86827 | DISCOVERY | 415.7030029 | 9.42855835 | 44.08977359 | interferon (alpha, beta and omega) receptor 1 (IFNAR1) |
| 53 | 40727 | BG573885.1 | GE55241 | DISCOVERY | 1204.090942 | 28.16665649 | 42.74880629 | linker for activation of T cells (LAT) |
| 54 | 11635 | AI376607.1 | GE80662 | DISCOVERY | 106.1363525 | 2.5 | 42.45454102 | thymosin, beta 4, Y-linked (TMSB4Y) |
| 55 | 4403 | N26032.1 | GE56202 | DISCOVERY | 891.694458 | 21.96551514 | 40.595199 | programmed cell death 4 (neoplastic transformation inhibitor) (PDCD4), transcript variant 2 |
| 56 | 14949 | BX110547.1 | GE81738 | DISCOVERY | 1020.042969 | 25.26760864 | 40.36958872 | programmed cell death 10 (PDCD10), transcript variant 1 |
| 57 | 51004 | BM670853.1 | GE59115 | DISCOVERY | 345.9705811 | 8.725006104 | 39.65276092 | tumor necrosis factor (ligand) superfamily, member 10 (TNFSF10) |
| 58 | 17177 | AI274757.1 | GE54607 | DISCOVERY | 1033.54187 | 26.16049194 | 39.50773832 | tumor necrosis factor superfamily, member 5-induced protein 1 (TNFSF5IP1) |
| 59 | 9938 | NM_152288.1 | GE87537 | DISCOVERY | 11.78378296 | 0.299987793 | 39.28087487 | interleukin 17D (IL17D) |
| 60 | 21487 | NM_006861.4 | GE58813 | DISCOVERY | 387.6266479 | 9.909088135 | 39.11829653 | programmed cell death 2 (PDCD2), transcript variant 1 |
| 61 | 37834 | BU608350.1 | GE57222 | DISCOVERY | 545.7602539 | 14.10638428 | 38.68888322 | proteasome (prosome, macropain) 26S subunit, non-ATPase, 1 (PSMD1) |
| 62 | 42661 | C04533.1 | GE60353 | DISCOVERY | 1506.339355 | 39.14474487 | 38.4812664 | proteasome (prosome, macropain) subunit, beta type, 9 (large multifunctional protease 2) (PSMB9), transcript variant 1 |
| 63 | 42680 | AW449970.1 | GE80314 | DISCOVERY | 1616.487305 | 42.02856445 | 38.46163498 | proteasome (prosome, macropain) 26S subunit, ATPase, 4 (PSMC4), transcript variant 1 |

This experiment revealed the facts described below, and it was clarified that the artificially synthesized peptide also significantly influenced the expression of human cancer-related gene to induce cancer, as in the peptide derived from the original cell line.

A. Enhanced Gene

1. Oncogene

Expression of oncogenes of cranial neuroblastoma, lung cancer, parotid gland tumor, breast cancer, colon cancer, renal cancer, ovarian cancer, melanoma, T-cell leukemia, B-cell leukemia, and so on were enhanced in the range of 47 to 1.7 times the baseline expression thereof. Expression of carcinogenic genes such as RAS, RAB, v-myc, and mab were also enhanced in the range of 6.7 to 1.7 times the baseline expression thereof. Additionally, expression of cell growth factor such as a platelet-derived growth factor was enhanced.

2. Immune System Gene

Expression of TNF, which is an inflammatory factor, was not enhanced, but expression of most of important factors as an operating factor for the humoral immunity mechanism, which is the opposite side of anti-tumor immunity, was enhanced.

B. Suppressed Gene

1. Cancer-Suppressing Gene

Every cancer-suppressing gene was significantly suppressed: Expression of heat shock protein relating to cancer antigen-induction was suppressed in the range of 1/461 to 1/116 of the baseline expression thereof, and expression of a tumor rejection antigen was suppressed in the range of 1/86 to 1/81 of the baseline expression thereof. Expression of a gene relating to inhibition of metastasis of breast cancer was suppressed to 1/60, expression of a gene relating to inhibition of leukemia was suppressed to 1/43, and expression of RAS suppressor protein gene was suppressed to 1/43.

2. Immune System Gene

The expression of genes relating to anti-tumor immunity was highly suppressed as follows:

suppression of a gene relating to construction of thymus tissues or production of a thymic hormone;

suppression of a function and a construction factor of T-cell which is important in inhibition of cancer;

suppression of a function and construction of NK-cell;

suppression of production of a factor for killer-cell-secretion;

suppression of an apoptosis factor relating to cellular suicide;

suppression of a factor relating to cell adhesion in cell apoptosis;

suppression of production of antineoplastic interferon; and suppression of expression of a cell organelle, an enzyme system, and a major histocompatibility complex (MHC) relating to induction of a cancer antigen.

(b) The peptide obtained in Example 3 was added to a culture medium (10 to 100 µg peptide/$1 \times 10^7$ monocytes) for human normal peripheral blood monocytes extracted from subjects shown in Table 5 below, and they were cocultured for 7 hr. Then, total mRNA was extracted from the monocytes, and the amount of the total mRNA was measured and compared to that of the total mRNA before the treatment with the peptide. Table 5 shows the results.

TABLE 5

Effect of the artificially synthesized peptide on total mRNA amount of peripheral blood monocytes

| NAME | pre total RNA (µg/ml) | post total RNA (µg/ml) | post/ pre (%) | reduction ratio (%) | |
|---|---|---|---|---|---|
| H.S. | 45.875 | 0.958 | 2 | 98 | Healthy subject (smoker) |
| M.S. | 20.779 | 9.188 | 44.2 | 55.8 | Healthy subject (smoker) |
| E.E. | 69.622 | 7.735 | 11.1 | 88.9 | Healthy subject (side-stream smoke) |
| S.G. | 61.145 | 16.562 | 27 | 73 | Healthy subject |
| H.T. | 66.804 | 14.742 | 22 | 78 | Healthy subject (side-stream smoke) |
| M.O. | 58.076 | 19.551 | 33.6 | 66.4 | Healthy subject (side-stream smoke) |
| M.A. | 52.318 | 17.681 | 33.7 | 66.3 | Healthy subject |
| K.K. | 8.078 | 1.757 | 21.7 | 78.3 | Cancer patient received chemotherapy and radiotherapy |

Samples are equivalent to $1 \times 10^7$ peripheral blood monocytes.
Treatment time with the peptide: 7 hr
The processes for collecting total RNA are the same as those in Example 4.

With referred to the results shown in Table 5, the total mRNA in H.S. and E.E. were significantly decreased. H.S. was an addicted smoker who has smoked for more than ten years. With respect to M.S., the reduction ratio of total mRNA was low, but the pre-total mRNA amount itself was also low, which has been caused by smoking over a long period of time. E.E. was not a smoker, but father of E.E. was an addicted smoker. Therefore, it was assumed that the decrease in the total mRNA was caused by passive smoking over a long period of time. Both H.T. and M.O. were passive smokers, and the reactivity to the peptide was accelerated in proportion to degree of the passive smoking (H.T.>M.O.). In K.K., the reduction ratio was low and the pre-total mRNA amount was significantly small. This subject was a cancer patient who has already received an anticancer agent and irradiation at the maximum possible dose. Therefore, the general gene translation was significantly impaired; which caused the result entirely different from that in healthy subjects. The results shown in Table 5 show that the cancer diagnosis can be efficiently performed by analyzing the changing ratio of total mRNA amounts before and after the treatment with the peptide of the present invention.

Example 5

Detection of the Peptide of the Present Invention in Cancer Cells and Influence of the Peptide on Normal Cells In order to examine influences at a gene level of the peptide on normal cells, RT-PCR was performed by adding the peptide artificially synthesized in Example 3 to the normal cells.
(Method and Result)
(1) Normal cells were treated with the artificially synthesized peptide for 7 hr as follows:

| | No. of Cells | Peptide Amount |
|---|---|---|
| Kidney mesangium cell: (ACBRI-1376; Applied Cell Biology Research Institute) | $1.25 \times 10^6$ | 12.5 µg |
| Skin fibroblast cell: (Catlog2F0-C25; Cell Systems) | $4.0 \times 10^6$ | 40.0 µg |
| Pancreatic epithelial cells: (ACBRI515; Applied Cell Biology Research Institute) | $1.05 \times 10^7$ | 105.0 µg |
| Peripheral blood monocytes: | | |
| H.S. | $1.25 \times 10^7$ | 12.5 µg |
| M.S. | $1.20 \times 10^7$ | 12.0 µg |
| E.E. | $1.40 \times 10^7$ | 14.0 µg |

(Kidney mesangium cells, skin fibroblast cells, and pancreatic epithelial cells: 100 µg peptide/$1.0 \times 10^7$ cells, peripheral blood monocytes: 10 µg peptide/$1.0 \times 10^7$ cells)

Then, total RNA was extracted from the above-treated normal cells, untreated normal cells, and squamous-cell carcinoma cells by using an RNA extraction kit (QIAGEN). The numbers of the treated cells and the untreated cells were the same.

|  | No. of Cells | RNA Amount |
| --- | --- | --- |
| Kidney mesangium cell: (ACBRI-1376; Applied Cell Biology Research Institute) | $1.25 \times 10^6$ | 30 μg |
| Skin fibroblast cell: (Catlog2F0-C25; Cell Systems) | $4.0 \times 10^6$ | 30 μg |
| Pancreatic epithelial cells: (ACBRI515; Applied Cell Biology Research Institute) | $1.05 \times 10^7$ | 30 μg |
| Peripheral blood monocytes: |  |  |
| H.S. | $1.25 \times 10^7$ | 60 μg |
| M.S. | $1.20 \times 10^7$ | 60 μg |
| E.E. | $1.40 \times 10^7$ | 60 μg |
| Cervical carcinoma cells (HeLa): | $1.60 \times 10^7$ | 60 μg |

Reverse transcription was performed by using 30 μg of each extracted total RNA to generate cDNA pools.

PCR was conducted using each of the cDNA pools as templates.

The condition for the PCR was as follows:

PCR buffer: 6 μl
dNTP: 2 μl
Primer Fw (11 amino acids or 7 amino acids): 1 μl
Primer Rv (oligo dT): 1 μl
dH2O: 9.5 μl
taq: 0.5 μl
Sample (RT products): 10 μl
(Total: 30 μl)
PCR: 45 cycles
Initial denaturation: at 94° C. for 5 min
Denaturation: at 94° C. for 30 sec
Annealing: at 55° C. for 30 sec
Extension: at 72° C. for 1 min (2) Each of the PCR products was applied to electrophoresis and detected by using a fluorescence label.

(a) FIGS. 2A and 2B show the results when the full-length peptide (11 amino acids) of the present invention was used as the primer in the PCR.

The results are as follows:

(i) Lanes 2 and 3 in FIG. 2A show the results of original UTC-8 cell samples which were not treated with the peptide of the present invention. The original UTC-8 cell samples stably expressed the gene of the preset invention.

Lane 4 in FIG. 2A shows the result of a cervical carcinoma cell sample, wherein a smear was observed. This means that the sample includes various sizes of genes which are complementary to the gene encoding the peptide of the present invention. Namely, the expression pattern of the gene was significantly changed in the cervical carcinoma cell sample by the treatment with the peptide of the present invention. Therefore, samples showing such a reaction pattern are thought to have a tendency of canceration.

(ii) On the basis of the results above, samples on each lane were examined. In some samples (Lanes 5 and 6 of FIG. 2A, lanes 4 and 5, lanes 6 and 7, and lanes 8 and 9 in FIG. 2B), the original stable gene pattern was changed to a pattern having a broadened smear by the treatment with the peptide of the present invention. Such samples were determined to have a tendency of canceration. Actually, the blood sample of the lanes 5 and 6 of FIG. 2A was obtained from a young man who had smoked for more than 10 years. Though the samples were normal cells, they had a high sensitivity to the peptide. It is thought that such a high sensitivity is caused by that these cells were, as in the peptide of the present invention, extracted from epithelial cells and were derived from a tissue in an early stage. Therefore, the gene expression is not fixedly stable, and the unstable gene expression is involved in the acuity sensitivity against a highly disturbing factor from the outside such as the peptide of the present invention.

(iii) On the contrary, in the sample of lanes 2 and 3 of FIG. 2B, gene mutation was hardly induced even if the sample was treated with the peptide of the present invention. This sample is thought to have a characteristic to rarely get cancer. Actually, the sample was obtained from a healthy young man in twenties.

(b) FIGS. 3A and 3B show the results when a DNA encoding an amino acid sequence (7 amino acids) at positions 1-7 of the peptide of the present invention was used as a primer in the PCR.

The results are as follows:

(i) Smears were observed in an UTC-8 cell sample shown in lane 3 of FIG. 3A and in a cervical carcinoma cell sample shown in lane 4 of FIG. 3A, as in the results when the full sequence was examined in the above-mentioned (a).

(ii) In the samples of lanes 2 and 3, lanes 4 and 5 of FIG. 3B, smears were not observed even if the samples were treated with the peptide of the present invention, and normal patterns were observed.

(iii) In the samples of lanes 5 and 6, lanes 7 and 8 of FIG. 3A and lanes 6 and 7, lanes 8 and 9 of FIG. 3B, gene expression patterns were significantly changed before and after the treatment with the peptide of the present invention.

As shown above, it was clarified that a tendency of canceration in normal cells can be determined by comparing changes in gene patterns induced by treating the cells with the peptide of the present invention.

In particular, when the PCR was performed by using the 11-amino acid primer (full sequence), a difference in the band patterns was observed in the peripheral blood sample (H.S.) and the skin fibroblast sample, and a difference in a position having a high concentration was observed in the kidney mesangium sample and the pancreatic epithelial sample, though it was a smear. When the PCR was performed by using the 7-amino acid primer (partial sequence), the band pattern of the pancreatic epithelial sample treated with the peptide for 7 hr was similar to that of the UTC-8 cell sample used as a control, and a difference in the band patterns was observed in the pancreatic epithelial sample by the treatment with the peptide for 7 hr.

A possible explanation for causes of such significant effects is that the UTC-8 cell is a cancer cell of epithelium and the peptide of the present invention is derived from UTC-8 cell line.

Therefore, epithelial cells are the most suitable samples for the measurement of a tendency of canceration using the peptide of the present invention, but it was proved that non-epithelial cell samples including peripheral blood, which can be most easily obtained in clinical practice, were useful for the diagnosis of a gene change in the full sequence.

Example 6

Exhaustive Gene Analysis of 55000 Genes by Using a DNA Chip System (Codelink System)

Characteristics of the peptide of the present invention were clarified by conducting the analysis described below in order to examine effects of the peptide on gene expression of normal cells.

(1) Preparation of Target cRNA

Normal lymphocytes were treated with the peptide of the present invention as in Examples 4 and 5, and the gene expression was compared to that of untreated lymphocytes by using a DNA chip system (Codelink System). In this examination, cRNA derived from bacteria was used as a positive control. Total RNA was extracted by using the QIAGEN RNA extraction kit used in Example 5. The total RNA (5 to 10 μg) was subjected to reverse transcription using an oligo-dT primer having a T7 RNA polymerase promoter region as a reverse primer to generate a pool of cDNAs complementary to the mRNAs. The condition for the reverse transcription was the same as that in Example 5. After second-strand cDNA synthesis, the treatment with T7 RNA polymerase and biotinylated rNTPs was performed in vitro transcription (IVT) reaction at 37° C. for 14 hr to obtain biotin-labeled cRNA. The amount of the cRNA was measured with a spectrophotometer to confirm at least 10 μg of the cRNA.

(2) Hybridization to Codelink Slide

The cRNA (10 μg) obtained in the above (1) was fragmentized and mixed with hybridization buffer, and then thermally denatured. This mixture solution was poured into a Codelink slide on which 55000 genes were immobilized, and a hybridization reaction was performed at 37° C. for 18 hr using an INNOVA 4080 shaker.

(3) Staining and Detection

The hybridization chamber was removed and the plate was washed at 46° C. for 1 hr. The hybridization was detected with Cy5-streptavidin (1:500 dilution, at room temperature for 30 min). The plate was further washed at a room temperature for 5 min 5 to 6 times and then washed with 0.05% Tween 20. The plate was dried by using a centrifuge for titer plates.

(4) The plate was scanned with an Arra WORK scanner with a PMT value of 600 at a resolution of 10 μm.

(5) The result was analyzed by exclusive software for the Codelink analysis. The software used was 1. Batch Submission 2 and 2. Codelink Expression 2.

Cancer-inducing expression status of cancer-related genes was observed in this experiment too, as in the results shown in Tables 1, 2, and 3.

Example 7

Examination of Antibody Against the Peptide for Cytotoxic Activity on Human Cancer Cells Monoclonal antibody (prepared by using BALB/c mouse) against the peptide of the present invention was examined for cytotoxic activity on various human cancer cell lines shown in FIG. 4: Each cancer cell line was seeded in a 96-well plate at $1\times10^4$ cells/well, and cultured in 5% $CO_2$ for 4 days to confirm that the cancer cells proliferated and adhered to the bottom surface of the plate so as to cover more than 80% of the surface area. The culture medium was removed by aspiration, and then 30 μl of the monoclonal antibody was added to each well under ice-cooling so that the surfaces of the cancer cells were brought into contact with the culture medium containing the monoclonal antibody. Then, the cancer cells were cultured under ice-cooling for 1 hr. As a control, each cancer cell line was also cultured in PBS buffer not containing the monoclonal antibody. Cytotoxic activity of the monoclonal antibody was examined by comparing the cancer cells treated with the monoclonal antibody with those of the control, and viability of the cell was determined by Trypan Blue staining. In the control, no substantial detachment of the cells from the bottom surface of the plate was observed; hence, cytotoxicity was not observed. On the contrary, in the cancer cells treated with the monoclonal antibody against the peptide of the present invention, detachment of the cells was observed in cancer cells shown in FIG. 4; hence, cytotoxic activity of the monoclonal antibody was observed. In addition, the detachment of the cancer cells was immediately induced by the addition of the monoclonal antibody, and the cancer cells were killed by the activity of the monoclonal antibody within only one hour. The photograph in the right of FIG. 4 shows human pancreatic cancer cells stained with FITC-labeled monoclonal antibody No. 1 of the present invention. These human pancreatic cancer cells died after this treatment.

Example 8

Immunosuppressive Agent Reducing Rejection in Transplantation

The experiment using the DNA chip proved that the peptide (SEQ ID NO: 1) had an ability to activate a cancer-related gene, and further suggested clinical usefulness of the cellular immunity-inhibition activity of the peptide. Then, the cellular immunity-inhibition activity of the peptide was examined from the viewpoint of activity for preventing rejection in skin transplantation.

The peptide of the present invention was administered to mice who have received skin transplantation according to the schedule shown in Table 6.

TABLE 6

| Days from Transplantation | Transplantation | Administration of Peptide |
|---|---|---|
| −3 | | Administration |
| −2 | | Administration |
| −1 | | Administration |
| 0 | Operation | |
| 1 | | |
| 2 | | Administration |
| 3 | | Administration |
| 4 | | |
| 5 | | |
| 6 | | |
| 7 | | Administration |
| 8 | | |
| 9 | | |
| 10 | | |
| 11 | | |
| 12 | | |
| 13 | | |
| 14 | | Administration |
| 15 | | |
| 16 | | |

Subject: skin of the back of a C57Black/6N mouse was transplanted to the back of a BALB/c mouse
Administration route: subcutaneously administered into the neck
Administration amount: 50 μg peptide/0.1 ml/mouse
Number of the subject: 6

The results show that, in the cross-transplantation of skin of the back of a C57Black/6N mouse to the back of a BALB/c mouse, the rejection in the skin transplantation was suppressed and skin graft survival was prolonged by intermittently administering the peptide at a very low amount of 50 μg peptide/0.1 ml/mouse through a subcutaneous route which is a most gentle administration (see the progress shown by the graph in FIG. 5). Namely, in the control, skin rejection occurred 7 days after the skin transplantation and the transplanted skin was rejected and was lost within 10 days after the transplantation in all 6 mice as shown in a photograph (control G1) of mice at bottom right in FIG. 5. On the contrary, in the mice administered with the peptide, skin rejection occurred 12 days after the transplantation; which was a 5 day delay. Furthermore, the transplanted skin of one mouse was survived for 14 days after the transplantation as shown in a photograph (treatment G1) at upper right in FIG. 5. Though the transplanted skin was lost in all mice on the 15th day from the date of the transplantation, a delay in the rejection in skin transplantation was observed.

Therefore, it was proved that the peptide can be used as an immunosuppressive agent by investigating administration dosage and route to increase efficiency thereof.

What is claimed is:

1. A diagnostic kit for determining tendency of canceration or malignancy of cancer, wherein the kit comprises
   (i) a peptide having an ability to activate a cancer-related gene, wherein the peptide is obtained from cell membrane surfaces of human squamous-cell carcinoma cells and comprises the amino acid sequence represented by SEQ ID NO: 1, and
   (ii) a polynucleotide comprising a nucleotide sequence encoding the eleven contiguous amino acids of the amino acid sequence of a peptide having an ability to activate a cancer-related gene, wherein the peptide is obtained from cell membrane surfaces of human squamous-cell carcinoma cells and consists of the amino acid sequence represented by SEQ ID NO: 1.

2. The diagnostic kit according to claim 1 further comprising at least one marker gene selected from the group consisting of:
   Ras oncogene family;
   v-crk avian sarcoma virus CT10 oncogene homolog lactate dehydrogenase B;
   Placental growth factor;
   Interleukin 8;
   MAS1, activator of S phase kinase;
   v-raf;
   v-fms;
   v-rel;
   IT-STC;
   GRO1;
   Hepatoma-derived growth factor;
   Vascular endothelial growth factor;
   Bone morphogenic protein 3;
   Squamous-cell carcinoma antigen recognized by T cell;
   Interleukin-1 beta;
   Conserved gene amplified in osteosarcoma; and
   Lymphoid blast crisis oncogene.

3. A diagnostic kit for determining tendency of canceration or malignancy of cancer, wherein the kit comprises
   (i) a peptide having an ability to activate a cancer-related gene, wherein the peptide is obtained from cell line UTC-8 (FERM BP-08611) established from human squamous-cell carcinoma; and the peptide shows a detectable peak at a detection wavelength of 214 nm in samples collected during gel filtration of an extract of the cell line, and
   (ii) a polynucleotide comprising a nucleotide sequence encoding the eleven contiguous amino acids of the amino acid sequence of a peptide having an ability to activate a cancer-related gene, wherein the peptide is obtained from cell membrane surfaces of human squamous-cell carcinoma cells and consists of the amino acid sequence represented by SEQ ID NO: 1.

4. The diagnostic kit according to claim 3 further comprising at least one marker gene selected from the group consisting of:
   Ras oncogene family;
   v-crk avian sarcoma virus CT10 oncogene homolog lactate dehydrogenase B;
   Placental growth factor;
   Interleukin 8;
   MAS1, activator of S phase kinase;
   v-raf;
   v-fms;
   v-rel;
   v-src;
   GRO1;
   Hepatoma-derived growth factor;
   Vascular endothelial growth factor;
   Bone morphogenic protein 3;

Squamous-cell carcinoma antigen recognized by T cell;
Interleukin-1 beta;
Conserved gene amplified in osteosarcoma; and
Lymphoid blast crisis oncogene.

5. The diagnostic kit according to claim 1, wherein the peptide (i) in the kit consists of the amino acid sequence represented by SEQ ID NO: 1.

* * * * *